(12) United States Patent
Webel et al.

(10) Patent No.: US 9,352,011 B2
(45) Date of Patent: *May 31, 2016

(54) METHOD AND COMPOSITION FOR SYNCHRONIZING TIME OF INSEMINATION

(71) Applicant: JBS United Animal Health II LLC, Sheridan, IN (US)

(72) Inventors: Stephen K. Webel, Baylis, IL (US); Mark E. Swanson, Princeton Junction, NJ (US)

(73) Assignee: JBS United Animal Health II LLC, Sheridan, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/532,419

(22) Filed: Nov. 4, 2014

(65) Prior Publication Data

US 2015/0057225 A1 Feb. 26, 2015

Related U.S. Application Data

(63) Continuation of application No. 13/265,307, filed as application No. PCT/US2010/032258 on Apr. 23, 2010, now Pat. No. 8,905,913.

(60) Provisional application No. 61/172,009, filed on Apr. 23, 2009.

(51) Int. Cl.
*A61B 17/43* (2006.01)
*A61K 38/00* (2006.01)
*A61K 38/09* (2006.01)
(Continued)

(52) U.S. Cl.
CPC ............... *A61K 38/09* (2013.01); *A61D 19/00* (2013.01); *A61K 9/0034* (2013.01); *A61K 9/06* (2013.01); *A61K 38/24* (2013.01); *A61K 47/14* (2013.01); *A61K 47/38* (2013.01)

(58) Field of Classification Search
CPC ....... A61K 38/09; A61K 38/24; A61D 19/00; A61B 17/425
USPC .............................. 600/33–35; 514/10.1, 10.3
See application file for complete search history.

(56) References Cited

U.S. PATENT DOCUMENTS 3,860,701 A   1/1975   Short
3,991,750 A   11/1976  Vickery
(Continued)

FOREIGN PATENT DOCUMENTS

CN   1913924     2/2007
GB   2 166 951   5/1986
(Continued)

OTHER PUBLICATIONS

Ramakrishnappa et al., "GnRH in non-hypothalamic reproductive Tissue", Anim Reprod Sci 2005; 88:95-113.
(Continued)

*Primary Examiner* — John Lacyk
(74) *Attorney, Agent, or Firm* — Barnes & Thornburg LLP

(57) ABSTRACT

Methods and compositions for synchronizing the time of insemination in swine are described. More particularly, methods are described for synchronizing the time of insemination by administration of a composition comprising a hormone, wherein the swine is inseminated only one time after administration of the hormone, and wherein there is no heat detection.

60 Claims, 2 Drawing Sheets

(51) Int. Cl.

| | | |
|---|---|---|
| *A61K 38/24* | (2006.01) | |
| *A61K 47/38* | (2006.01) | |
| *A61K 9/00* | (2006.01) | |
| *A61K 47/14* | (2006.01) | |
| *A61K 9/06* | (2006.01) | |
| *A61D 19/00* | (2006.01) | |

(56) References Cited

U.S. PATENT DOCUMENTS

| | | |
|---|---|---|
| 4,005,063 A | 1/1977 | Gendrich et al. |
| 4,008,209 A | 2/1977 | Fujino et al. |
| 4,400,316 A | 8/1983 | Katsuragi et al. |
| 4,732,763 A | 3/1988 | Beck et al. |
| 4,756,907 A | 7/1988 | Beck et al. |
| 4,780,451 A | 10/1988 | Donaldson |
| 4,804,626 A | 2/1989 | Bellet et al. |
| 4,931,279 A | 6/1990 | Bawa et al. |
| 4,975,280 A | 12/1990 | Schacht et al. |
| 5,180,711 A | 1/1993 | Hodgen |
| 5,236,704 A | 8/1993 | Fujioka et al. |
| 5,418,228 A | 5/1995 | Bennick |
| 5,434,136 A | 7/1995 | Mathias |
| 5,434,146 A | 7/1995 | Labrie et al. |
| 5,444,167 A | 8/1995 | Pettersson |
| 5,512,303 A | 4/1996 | Garza Flores et al. |
| 5,585,370 A | 12/1996 | Casper |
| 5,589,457 A | 12/1996 | Wiltbank et al. |
| 5,605,702 A | 2/1997 | Teillaud et al. |
| 5,633,014 A | 5/1997 | Garza Flores et al. |
| 5,650,173 A | 7/1997 | Ramstack et al. |
| 5,686,097 A | 11/1997 | Taskovish et al. |
| 5,688,506 A | 11/1997 | Grimes et al. |
| 5,747,058 A | 5/1998 | Tipton et al. |
| 6,028,057 A | 2/2000 | Burns |
| 6,051,558 A | 4/2000 | Burns et al. |
| 6,087,352 A | 7/2000 | Trout |
| 6,469,139 B1 | 10/2002 | Roitt et al. |
| 6,908,623 B2 | 6/2005 | Deaver et al. |
| 7,205,281 B2 | 4/2007 | Lauderdale |
| 7,456,207 B2 | 11/2008 | Bentley et al. |
| 8,530,419 B2 | 9/2013 | Lauderdale |
| 8,905,913 B2 | 12/2014 | Webel |
| 8,927,496 B2 | 1/2015 | Lauderdale |
| 8,937,044 B2 | 1/2015 | Lauderdale |
| 9,018,165 B2 | 4/2015 | Lauderdale |
| 2004/0266697 A1 | 12/2004 | McSweeney |
| 2005/0130894 A1 | 6/2005 | Lauderdale |
| 2006/0264372 A1 | 11/2006 | Webel |
| 2007/0031500 A1 | 2/2007 | Cherif-Cheikh |
| 2007/0173450 A1 | 7/2007 | Lauderdale |
| 2007/0197435 A1 | 8/2007 | Webel |
| 2009/0036384 A1 | 2/2009 | Bell |
| 2010/0312137 A1 | 12/2010 | Gilmour |
| 2012/0046519 A1 | 2/2012 | Webel |
| 2013/0041210 A1 | 2/2013 | Lauderdale |
| 2013/0085321 A1 | 4/2013 | Lauderdale |
| 2013/0085322 A1 | 4/2013 | Lauderdale |
| 2014/0155327 A1 | 6/2014 | Lauderdale |
| 2015/0087587 A1 | 3/2015 | Lauderdale |
| 2015/0306169 A1 | 10/2015 | Webel et al. |

FOREIGN PATENT DOCUMENTS

| | | |
|---|---|---|
| SU | 573159 | 9/1977 |
| WO | WO 97/32572 | 9/1997 |
| WO | WO 97/37642 | 10/1997 |
| WO | WO 97/45113 | 12/1997 |
| WO | WO 98/53837 | 12/1998 |
| WO | WO 99/42110 | 8/1999 |
| WO | WO 00/78335 | 12/2000 |
| WO | WO 2005/035717 | 4/2005 |
| WO | WO 2008/018796 | 2/2008 |
| WO | WO 2010/124220 | 10/2010 |

OTHER PUBLICATIONS

Wahner and Huhn, "New aspects of the Management of Reproduction in Pig", Reprod Dom Anim. 1996;31:477-482.

Barb et al., "Evaluation of the saber delivery system for the controlled release of deslorelin: Effect of dose in estrogen primed ovarectomized gilts", Proceed. Int'l. Symp. Control. Rel. Bioacr. Mater., 26: 1170-1171 (1999).

Betteridge and Raeside, "Observation of the ovary by peritoneal cannulation in pigs", Res. Vet. Sci. 3:390-398 (1962).

Britt et al., "Induction of fertile estrus in perpuberal gilts by treatment with a combination of pregnant mare's serum gonadotrophin and human chorionic gonadotropin", J. Anim. Sci., 67:1148-53 (1989).

Brussow et al., "Control of ovulation with a GnRH analog in gilts and sows", Theriogenology, 46:925-934 (1996).

Burns and Douglas, "Effects of daily administration of estradiol-17 ($\beta$ on follicular growth, ovulation, and plasma hormones in mares", Biology of Reproduction, 24:1026-1031 (1981).

Burns et al., "Evaluation of biodegradable microspheres for the controlled release of progesterone and estradiol in an ovulation control program for cycling mares", J. Equine Vet. Sci. 13(9):521-24 (1993).

Cook et al., "Effects of the exogenous estradiol treatment in cyclic mares following PGF induced luteal regression", Proceeding of the $13^{th}$ Equine Nutrition & Physiology Symposium, Abstract 126, 1993.

De Rensis et al., "Fertility of sows following artificial insemination at a gonadotrophin-induced estrus coincident with weaning", Animal Reproduction Science, 76:245-250 (2003).

Donbrow, ed., "Microcapsules and Nanoparticles in Medicine and Pharmacy", (CRC Press, Boca Raton 1992) (Table of Contents only).

Du Mesnil et al., "Reproductive physiology and artificial insemination in pigs", Vet Rec., 87:562-568 (1970).

Flowers and Alhusen, "Reproductive performance and estimates of labor requirements associates with combinations of artificial insemination and natural service in swine", J. Animal Science, 70:615-621 (1992).

Geisert et al., "Length of pseudopregnancy and pattern of uterine release as influenced by time and duration of estrogen administration in the pig", J. Reprod. Fert., 79:163-72 (1987).

Jackson and Hutchinson, "Slow release formulations of prostaglandin and luteolysis in the pig", Veterinary Record, 106:33-34 (1980).

Martinat-Botte et al., "Control of pig reproduction in a breeding programme", J. Reprod. Fert. Suppl., 33:211-228 (1985).

Niswender et al., "Radioimmunoassay of serum levels of lutenizing hormone throughtout the estrous cycle in pigs", Endocrinology, 87:576-580 (1970).

Peters et al., "Effect of gonadotrophin-releasing hormone on the fertility of sows kept outdoors", Vet. Record, 147:649-652 (2000).

Polge et al., "Synchronisation of ovulation and artificial insemination in pigs", Veterinary Record, 83, 136-142 (1968).

Prokofeva, "Composition for oestrus cycle control in sows-continaing hydroxyl-progesterone caproste, oestradiol valerate, oil, and benzoate to improve heat synchronization", Derwent Publications, Limited SU-549118 (1977).

Pusateri et al., "Maternal Recognition of Pregnancy in Swine.I. Minimal Requirement for Exogenous Estradiol-17B to Induce Either Short or Long Pseudopregnancy in Cycling Gilts", Biol. Reproduction, 55:582-89 (1996).

Sechin et al., "Effect of equine chorionic gonadatropin on weaning to first service interval and litter size of female swine", Theriogenology, 51:1175-1182 (1999).

Sheffield et al., "Effect of estradiol and relaxin on collagen and non-collagen protein sythesis by mammary fibroblasts", Life Sci., 35 (22): 2199-2203 (1984).

Soede et al., "In Synchronized pigs, the duration of ovulation is not affected by insemination and is not a determinant for early embryonic diversity", Theriogenology, 39:1043-1053 (1993).

Stevenson et al., "Role of the Ovary in Controlling Luteinizing Hormone, Follice Stimulating Hormone, and Prolactin Secretion During and After Lactation in Pigs", Biol. Reproduction, 24:341-53 (1981).

Stork, M.G., "Seasonal reproduction inefficiency in large pig breeding units in Britain", Veterinary Record, 104:49-52 (1979).

(56) References Cited

OTHER PUBLICATIONS

Tilton et al., "Evaluation of Response to Hormonal Therapy in Prepubertal Gilts of Different Genetic Lines", J. Anim. Sci., 73:3062-68 (1995).
Ulberg et al., "The effects of progesterone upon ovarian function in gilts", J. Animal Sci., 10:665-671 (1951).
Van Der Meulen et al., "Effects of intra-uterine oestradiol-17 beta administration of inter-oestrous interval in the pig", Animal Reproduction Science, 24:305-313 (1991).
Gordon, I.R., Controlled Reporduction in Pigs CAB International: Wallingford, Oxon, UK; New York, ISBN:0851991165 (table of contents only) (1997).
Asdell, Patterns of Mammalian Reproduction, 2nd ed., Cornell University Press, Ithaca, USA, pp. 670 (1964).
Dziuk, Reproduction in the pig. In: Cupps, P.T. (ed.) Reproduction in Domestic Animals, 4th ed., Academic Press, New York, pp. 471-489 (1991).
Day, et al., Effect of intravaginal progesterone (P4) insert-porcine (IPI-P) on synchronization of estrus, ovulation rate, fertility and P4 blood levels in gilts. In: Control of Reproduction in the Female Pig. 30th Annual Meeting, American Association of Swine Practitioners, Workshop #6, St. Louis, Mo. Feb. 27, 1999, pp. 23-39 (ref. unavailable).
Estill et al., "Estrus sychronization of gilts using steriod-containing implants and a PGF2α analogue," *Society for Teriogenology Proceedings for Annual Meeting* (1997).
Webel, S.K. and B.N. Day. 1982. The control of ovulation. In: D.J.A. Cole and G.R. Foxcroft (Eds.) *Control of Pig Reproduction*. Butterworths, London. pp. 197-210.
Nissen et al., "The influence of time of insemination relative to time of ovulation on farrowing frequency and litter size in sows, as investigated by ultrasonography," *Theriogenology*, 47: 1571-1582 (1997).
Waberski et al., "Effect of time of insemination relative to ovulation on fertility with liquid and frozen boar semen," *Theriogenology*, 42: 831-840 (1994).
Soede et al., "Timing of insemination relative to ovulation in pigs: Effects on sex ratio of offspring," *Theriogenology*, 53: 1003-1011 (2000).
Knox et al., "Controlling Estrus and Ovulation", National Hog Farmer, Nov. 15, 2003, 18-20.
Knox et al., "Intravaginal administration of GnRH agonist gel advances time of ovulation and facilitates timed AI in weaned sows," 34th Annual AASV Meeting: Orlando, Florida, USA (2003), available at www.aasv.org.
Busch et al., "Investigations of Estrus Synchronization in swine with the Gestagen Altrenogest (Regumate)", Vet. Med. Monthly, 47:307-316 (1992).
Fleury et al., "Regulation of estrus and ovulation in cyclic mares with progesterone and estradiol biodegradable microspheres", J. Equine Vet. Sci., 13(9):525-28 (1993).
Knox et al., "Administration of P.G. 600 to Sows at Weaning and the Time of Ovulation as Determined by Transrectal Ultrasound", J. Animal. Sci., 79:796-802 (2001).
LaForest et al., "Effect of Topical Application of Estradiol-17B and PGE2 on PGE-binding sites in the Porcine Endometrium", Reprod. Nutr. Dev., 32(2): 93-104 (1992).
Dixon et al., "The effects of estradiol cypionate on expression of estrus in a follicular synchronization program," J. Animal Science, 82 (supp. 1): 369, W225 (2004).
Kirkwood, "Pharmacological intervention in swine reproduction", Swine Health Prod., 7(1): 29-35 (1999).
Langendijk, "Synchronization of ovulation with GnRH or hCG in weaned sows, without pre-treatment with eCG", J. Reprod. Fertil., Abstract Series No. 26, Abstract #93, p. 35 (2000).
Gerrits et al., "Effect of synchronization of estrus on fertility in gilts", J. Animal Sci., 21:1022 (1962).
Guthrie et al., "Treatment of pregnant gilts with a prostaglandin analogue, Cloprostenol, to control estrus and fertility", J. Reprod. Fert., 52:271-73 (1978).
Guthrie et al., "Changes in plasma estrogen, luteinizing hormone, follicle-stimulating hormone and 13, 14-dihydro-15-ketoprostaglandin F2 during blockade of luteolysis in pigs after human chorionic gonadotropin treatment", J. Anim. Sci., 57:993-100 (1983).
Hansel et al., "Corpora lutea of the large domestic animals", Biology of Reproduction, 8:222-245 (1973).
Hodson et al., "Effect of gonadotropin dose and postpartum status on induced ovulation and pregnancy in lactating sows", J. Animimal Sci., 52(4):688-695 (1981).
Howard, et al., "Prostaglandin F2 causes regression of an hCG induced corpus luteum before Day 5 of its lifespan in cattle," J. Reprod. Fert., 90:245-53 (1990).
Hunter and Polge, "Maturation of follicular oocytes in the pig after injection of human chorionic gonadotrophin," J. Repro. Fert. 12: 525-531 (1966).
Hunter, "Physiological factors influencing ovulation, fertilization, early embryonic development and establishment of pregnancy in pigs," Brit. Vet. J., 133: 461-470 (1977).
Hurtgen and Leman, "Seasonal influence on the fertility of sows and gilts," J Amer Vet. Med. Ass., 177: 631-635 (1980).
Betteridge and Raeside, "Investigation of Cervical Mucus as an indicator of ovarian activity in pigs," J. Reprod. Fertility., 3:410-421 (1962).
Coffey, "Manipulation of the Estrous Cycle in Swine," available t.ca.uky.edulagc/pubs/asc/asc15asc152.htm, 1110/2007.
Broaddus, "Insemination of diary cows without heat detection," Journal of Diary Science vol. 79, Suppl. 1, 1996.
Webel, "Estrus Control in Horses with a Progestin," #564, p. 385 (1975).
Webel, "Response of the Cycling Gilt to TRH," #566, p. 385 (1975).
Soede et al., "Effects of time of insemination relative to ovulation, as determined by ultrasonography, on fertilization rate and accessory sperm count in sows," Journal for Reproduction and Fertility (1995) 104, 99-106.
Larson et al., "Synchronization of estrus in replacement beef heifers using GnRH, prostaglandin F2-alpha (PG), and progesterone (CIDR): a multi-location study," J. Animal Science, 82(supp. 1): 369, W223 (2004).
Webel and Rippel, et al., "Ovulation in the pig with releasing hormones," J *Animal Science*, 41:385, Abstract No. 565 (1975).
Yavas, at al., "Postpartum acyclicity in suckled beef cows: A review", *Theriogenology*, 54(1):25255 (2000).
Yavas, at al., "Induction of ovulation in postpartum suckled beef cows: A review", *Theriogenology*, 54(1):1-23 (2000).
Roski et al., "Ovulatory and reproductive characteristics of sows treated with an intravaginal GnRh agonist gel", J. Anim. Sci., vol. 82 Supplement 1, Jul. 28, 2004.
Filicori, Drugs 1994; 48: 41-58.
Crowley, Annu Rev. Med. 1994; 45: 391-405.
Boime and Ben-Menahem, Recent Progr. Horm Res. 1999; 54: 271-288.
Garcia-Campayo and Boime, Trends Endocrinol. Metabl 2001; 12: 72-77.
PG600, MSD Animal Health, product sheet, http://www.msd-animal-health.ph/products/131_118602/productsdetails_131_118778, printed May 25, 2012.
Handelsman et al, "Pharmacokinetics of Gonadotropin-Releasing Hormone and Its Analogs", Endocrine Review, vol. 7, No. 1, 95-105 (1986).
Conn, "Gonadotropin-Releasing Hormone and Its Analogues", The New England Journal of Medicine, vol. 324, 93-103 (1991).
S. K. Webel, "Ovulation Control in the Pig", Easter School in Agriculture Science, 26th, 1978.
Roski, "Ovulatory and reproductive characteristics of sows treated with an intravaginal GnRH agaonist gel," Thesis, North Carolina State University, Raleigh, 2004.
Kim & Park, Journal of Controlled Release, 2002; 80: 69-77.
Bos et al., "Hydrogels for the Controlled Release of Pharmaceutical Proteins", Pharmaceutical Technology, 79:110-120 (2001).
Goodman & Gilman's The Pharmacological Basis of Therapeutics, Ninth Ed., 1996; From Benet et al., Chapter 1, Pharmacokinetics'; p. 8.

(56) References Cited

OTHER PUBLICATIONS

Gupta et al., DDT, 2002; 7: 569-579.
Wenzel et al., "Pluronic ® F127 gel formulations of Deslorelin and GnRH reduce drug degradation and sustain drug release and effect in cattle", J Controlled Release, 85: 51-59 (2002).
Baer et al., "The Effects of Intravaginal Applied GnRH-agonist on the Time of Ovulation and Subsequent Reproductive Performance of Weaned Multiparous Sows", Reprod Dom Anim 39, 293-297 (2004).
Belstra et al., "Factors affecting temporal relationships between estrus and ovulation in commercial sow farms", Animal Reproduction Science 84 (2004) 377-394.
Brussow et al., "Lutenizing hormone release after administration of the gonadotropin-releasing hormone agonist Fertilan (goserelin) for synchronization of ovulation of pigs", J. Anim. Sci. 2007, 85:129-137.
H. D. Guthrie, "Induction of Ovulation and Fertility in Prepuberal Gilts", J Anim Sci 1977, 45:1360-1367.
Guthrie et al., "Attempts to Induce Conception in Lactating Sows", J Anim Sci 1978, 47:1145-1151.
Baker et al., "Induction of Ovulation in Pigs with Gonadotrophin Releasing Hormone", J Anim Sci Dec. 1973, vol. 37, No. 6, 1376-1379. (summary only).
Langendijk et al., "Role of myometrial activity in sperm transport through the genital tract and in fertilization in sows", Reproduction (2002) 123, 683-690.
Tek et al., "The effect of Gonadotrophins on estrus induction and fertility in prepubertal gilts", Revue Med. Vet., 2003, 154, 2, 133-138.
Taibl et al., "Effect of Synchronizing Ovulation in Weaned Sows Using Ovugel with Single Fixed Time AI on Pregnancy Rate and Littler Size", VIII International Conference on Pig Reproduction, Jun. 1-3, 2009.
Madan et al., "In Situ Forming Polymeric Drug Delivery Systems", Indian J. Ph arm Sci., 71: 242-26 (2009).
Berger et al., Mol Cell Endocrinol. 1996; 125: 33-43.
Gooneratne et al., Can. J. Anim. Sci., 1989, 69:123-129.
Taibl, J.N., et al. "Induction of ovulation using a GnRH agonist for use with a fixed time AI in weaned sows", Theriogenology, 2008, 70(8), 1400.
Schneider, F., et al. "Gonadotropin-releasing hormone (GnRII) and its natural analogues: A review", Theriogenology, 2006, 66(4), 691-709.
European Search Report from European Patent Application No. 10767846.8 issued Apr. 11, 2013.
Knox et al., Intravaginal administration of GnRH agonist-gel advances time of ovulation and facilitates timed AI in weaned sows; presented at the $34^{th}$ Proceedings of the American Association of Swine Veterinarians, Mar. 2003; 495-498.
Archived website downloaded Jan. 13, 2013 at web.archive.org/web/20040831011300/http://nationalhogfarmer.com/mag/farming (Aug. 31, 2004).
PCT International Search Report from PCT/US2013/072359 completed Feb. 28, 2014.
Brussow et al., "Studies on fixed-time ovulation induction in the pig," *Soc Reprod Fertil Suppl.*, 2009; 66:187-95.
Martinat-Botte et al., "Induction and synchronization of ovulations of nulliparous and multiparous sows with an injection of gonadotropin-releasing hormone agonist (Receptal)," *Theriogenelogy*, 2010; 73: 332-342.
Kraeling et al., "Failure of the orally active progestin, Regu-mate, to overcome confinement-induced delayed puberty in gilts," *Theriogenelogy*, 1982; 17:183-187.
Szabo et al., Acta Veterinaria Hungarica, 1991, 39: 1-11.

METHOD AND COMPOSITION FOR SYNCHRONIZING TIME OF INSEMINATION

CROSS REFERENCE TO RELATED APPLICATIONS

This application is a continuation of U.S. application Ser. No. 13/265,307, filed Oct. 19, 2011, which is a U.S. national counterpart application, under 35 U.S.C. §3.71(c), of International Application Serial No. PCT/US2010/032258 filed Apr. 23, 2010, which claims priority under 35 U.S.C. §119(e) to U.S. Provisional Application No. 61/172,009, filed Apr. 23, 2009, which are expressly incorporated by reference herein.

FIELD OF THE INVENTION

The invention relates to methods and compositions for synchronizing the time of insemination in an animal. More particularly, the invention relates to methods and compositions for synchronizing the time of insemination in a swine without heat detection.

BACKGROUND OF THE INVENTION

Gonadotropin-releasing hormone is a peptide of 10 amino acids and is also known as luteinizing-hormone releasing hormone (LHRH). Gonadotropin-releasing hormone is produced in the hypothalamus, and is responsible for the release of follicle-stimulating hormone and luteinizing hormone from the pituitary gland. Gonadotropin-releasing hormone is released from neurons in the hypothalamus, and plays a role in the complex regulation of follicle-stimulating hormone and luteinizing hormone release. Follicle-stimulating hormone and luteinizing hormone, in combination, regulate the functioning of the gonads to produce testosterone in the testes and progesterone and estrogen in the ovaries, and regulate the production and maturation of gametes. For example, follicle-stimulating hormone stimulates the growth and recruitment of immature ovarian follicles in the ovary, and luteinizing hormone triggers ovulation.

There are differences in gonadotropin-releasing hormone secretion between females and males. In males, gonadotropin-releasing hormone is secreted in pulses at a constant frequency, but in females the frequency of the pulses varies during the estrus cycle and there is a large surge of gonadotropin-releasing hormone just before ovulation. Gonadotropin-releasing hormone secretion is pulsatile in all vertebrates, and is necessary for correct reproductive function. Thus, gonadotropin-releasing hormone controls a complex process of follicular growth, ovulation, and corpus luteum maintenance in the female, and spermatogenesis in the male.

Gonadotropin-releasing hormone has been isolated and characterized as a decapeptide. Synthetic forms of gonadotropin-releasing hormone are available and modifications of the decapeptide structure of gonadotropin-releasing hormone have led to multiple gonadotropin-releasing hormone analogs that either stimulate (e.g., gonadotropin-releasing hormone agonists) or suppress (e.g., gonadotropin-releasing hormone antagonists) the release of the gonadotropins, such as luteinizing hormone and follicle-stimulating hormone.

It is important to commercial swine production to maximize reproductive efficiency to make swine production more profitable. There has been heavy reliance on daily heat detection of individual female swine with the associated labor costs devoted to manual detection of heat in the female swine based on daily checks of gilts or sows to achieve the best results with, for example, artificial insemination. Heat detection using labor intensive methods, such as daily checks, increases the probability of success with artificial insemination. Thus, devoting time, manual labor, and materials costs to daily checks for heat detection is necessary because it is difficult to predict the time of heat (i.e., the best time for insemination) without using methods requiring a daily regimen for monitoring heat detection. Accordingly, methods are needed to optimize the success of insemination of animals, without heat detection, to reduce the labor costs, and to increase the profitability of swine production.

SUMMARY OF THE INVENTION

Applicants have made the surprising discovery that controlling the time of ovulation via hormone administration can eliminate breeding based on estrus detection and allow a swine to receive only one insemination for optimal fertility and optimal cost expenditure. In one embodiment, a method of synchronizing time of insemination in a swine without heat detection is described. The method comprises the step of administering to the swine, on the fourth day after weaning, a dose of a hormone selected from the group consisting of a gonadotropin releasing hormone, a luteinizing hormone, a human chorionic gonadotropin, and combinations thereof, wherein the swine is inseminated only one time about 15 to about 24 hours after administration of the hormone and wherein there is no heat detection.

In the above described embodiment, the following features, or any combination thereof, apply. In the above described embodiment, 1) the swine can be a postpartum sow; 2) the swine can be a gilt; 3) the insemination can be an artificial insemination; 4) the insemination can be through natural breeding; 5) ovulation can be synchronized; 6) the hormone can be administered in an amount effective to stimulate ovarian follicle ovulation; 7) the dose of the hormone can be administered using a method selected from the group consisting of use of a deposition catheter, manual administration, and injection; 8) the swine can be inseminated about 15 to about 18 hours after administration of the hormone; 9) the swine can be inseminated about 18 hours after administration of the hormone; 10) the pregnancy rate of the swine can be increased relative to a swine to which no hormone is administered; 11) the litter size of the swine can be increased relative to a swine to which no hormone is administered; 12) the hormone can be administered to more than one swine; 13) the percentage of swine ovulating by about 48 hours after administration of the hormone can be increased relative to swine to which no hormone is administered; 15) the hormone can be administered intravaginally; 16) the hormone can be administered into the anterior vagina; 17) the hormone can be a gonadotropin releasing hormone receptor agonist; 18) the hormone can be a luteinizing hormone receptor agonist; 19) the hormone can be a human chorionic gonadotropin receptor agonist; 20) the hormone can be triptorelin; 21) the hormone can be a triptorelin salt; 22) the hormone can be synthetic; 23) the hormone can be in acetate form; 24) the hormone can be administered in a composition comprising a gel; 25) the gel can comprise a polysaccharide; 26) the polysaccharide can be selected from the group consisting of celluloses, dextrans, and alginates; 27) the gel can comprise a cellulose; and 28) the cellulose can be methylcellulose. Any combination of the embodiment of paragraph with 1-28, or any combination thereof, is contemplated.

In another embodiment, a kit comprising a dose of a hormone selected from the group consisting of a gonadotropin releasing hormone, a luteinizing hormone, a human chorionic gonadotropin, and combinations thereof is described. The kit further comprises instructions for use wherein the hormone is in a composition comprising a gel and the composition has a pH of about 5 to about 6.

In the embodiment described in paragraph, the following features, or any combination thereof, apply. In the embodiment described in paragraph, 1) the instructions can indicate that the hormone should be administered to a swine on about the fourth day after weaning and that the swine can be inseminated one time about 15 to about 24 hours after administration of the hormone; 2) the instructions can indicate that the insemination should be an artificial insemination; 3) the instructions can indicate that the insemination should be through natural breeding; 4) the kit can further comprise a deposition catheter, an applicator for manual administration, or a syringe; 5) the instructions can indicate that the swine should be inseminated about 15 to about 18 hours after administration of the hormone; 6) the instructions can indicate that the swine should be inseminated about 18 hours after administration of the hormone; 7) the instructions can indicate that the hormone should be administered intravaginally; 8) the instructions can indicate that the hormone should be administered into the anterior vagina; 9) the hormone can be a gonadotropin releasing hormone receptor agonist; 10) the hormone can be a luteinizing hormone receptor agonist; 11) the hormone can be a human chorionic gonadotropin receptor agonist; the hormone can be triptorelin; 12) the hormone can be a triptorelin salt; 13) the hormone can be synthetic; 14) the hormone can be in acetate form; 15) the gel can comprise a saccharide; 16) the gel can comprise a polysaccharide; 17) the polysaccharide can be selected from the group consisting of celluloses, dextrans and alginates; 18) the gel can comprise a cellulose; and 19) the cellulose can be methylcellulose. Any combination of the embodiment of paragraph with 1-19, or any combination thereof, is contemplated.

In another embodiment, a composition comprising a gonadotropin releasing hormone receptor agonist and a gel is described, wherein the composition has a pH of about 5.0 to about 6.0.

In the embodiment described in paragraph, the following features, or any combination thereof, apply. In the embodiment described in paragraph, 1) the composition can further comprise a preservative; 2) the preservative can be selected from the group consisting of methylparaben and propylparaben; 3) the composition can further comprise a stabilizer; 4) the stabilizer can be an L-amino acid; 5) the stabilizer can be L-methionine; 6) the gel can comprise a polysaccharide; 7) the polysaccharide can be selected from the group consisting of celluloses, dextrans and alginates; 8) the gel can comprise a cellulose; 9) the cellulose can be methylcellulose; 10) the composition can further comprise a tonicity agent; 11) the agonist can be triptorelin; 12) the composition can be combined with instructions for use; 13) the instructions in combination with the composition can indicate that a swine should be administered the agonist and that the swine should be inseminated one time about 15 to about 24 hours after administration of the agonist; and 14) the instructions can indicate that the swine should be inseminated one time about 18 hours after administration of the agonist. Any combination of the embodiment of paragraph with 1-14, or any combination thereof, is contemplated.

The following various embodiments are provided.

1. A method of synchronizing time of insemination in a swine without heat detection is described. The method comprises the step of administering to the swine, on the fourth day after weaning, a dose of a hormone selected from the group consisting of a gonadotropin releasing hormone, a luteinizing hormone, a human chorionic gonadotropin, and combinations thereof, wherein the swine is inseminated only one time about 15 to about 24 hours after administration of the hormone and wherein there is no heat detection.

2. The method of clause 1 wherein the swine is a postpartum sow.

3. The method of clause 1 wherein the swine is a gilt.

4. The method of clause 1 to 3 wherein the insemination is an artificial insemination.

5. The method of clause 1 to 4 wherein the insemination is through natural breeding.

6. The method of clause 1 to 5 wherein ovulation is synchronized.

7. The method of clause 1 to 6 wherein the hormone is administered in an amount effective to stimulate ovarian follicle ovulation.

8. The method of clause 1 to 7 wherein the effective amount of the hormone is about 10 µg to about 1000 µg.

9. The method of clause 1 to 7 wherein the effective amount of the hormone is about 10 µg to about 500 µg.

10. The method of clause 1 to 9 wherein the dose of the hormone is administered using a method selected from the group consisting of use of a deposition catheter, manual administration, and injection.

11. The method of clause 1 to 10 wherein the swine is inseminated about 15 to about 18 hours after administration of the hormone.

12. The method of clause 1 to 10 wherein the swine is inseminated about 16 to about 24 hours after administration of the hormone.

13. The method of clause 1 to 10 wherein the swine is inseminated about 18 to about 22 hours after administration of the hormone.

14. The method of clause 1 to 13 wherein the swine is inseminated about 18 hours after administration of the hormone.

15. The method of clause 1 to 14 wherein the pregnancy rate of the swine is increased relative to a swine to which no hormone is administered.

16. The method of clause 1 to 15 wherein the total number of healthy fetuses is increased relative to a swine to which no hormone is administered.

17. The method of clause 1 to 16 wherein the percentage farrowed is increased relative to a swine to which no hormone is administered.

18. The method of clause 1 to 17 wherein the total number of piglets born is increased relative to a swine to which no hormone is administered.

19. The method of clause 1 to 18 wherein the total number of piglets born per semen dose is increased relative to a swine to which no hormone is administered.

20. The method of clause 1 to 19 wherein the total number of piglets born per semen dose is increased relative to a swine inseminated following heat detection.

21. The method of clause 1 to 20 wherein the piglet index is increased relative to a swine to which no hormone is administered.

22. The method of clause 1 to 21 wherein the piglet index is increased relative to a swine inseminated following heat detection.

23. The method of clause 1 to 22 wherein the litter size of the swine is increased relative to a swine to which no hormone is administered.

24. The method of clause 1 to 23 wherein the hormone is administered to more than one swine.

25. The method of clause 1 to 24 wherein the percentage of swine ovulating by about 48 hours after administration of the hormone is increased relative to swine to which no hormone is administered.

26. The method of clause 1 to 25 wherein the hormone is administered intravaginally.

27. The method of clause 1 to 26 wherein the hormone is administered into the anterior vagina.

28. The method of clause 1 to 27 wherein the hormone is a gonadotropin releasing hormone receptor agonist.

29. The method of clause 1 to 28 wherein the hormone is a luteinizing hormone receptor agonist.

30. The method of clause 1 to 29 wherein the hormone is a human chorionic gonadotropin receptor agonist.

31. The method of clause 1 to 30 wherein the hormone is triptorelin.

32. The method of clause 1 to 31 wherein the hormone is a triptorelin salt.

33. The method of clause 1 to 32 wherein the gonadotropin releasing hormone has the formula pGlu-His-Trp-Ser-Tyr-Gly-Leu-Arg-Pro-GlyNH$_2$.

34. The method of clause 1 to 33 wherein the gonadotropin releasing hormone receptor agonist has the formula 37. The method of clause 1 to 36 wherein the hormone is synthetic.

38. The method of clause 1 to 37 wherein the hormone is in acetate form.

39. The method of clause 1 to 38 wherein the hormone is administered in a composition comprising a gel.

40. The method of clause 39 wherein the gel comprises a polysaccharide.

41. The method of clause 40 wherein the polysaccharide is selected from the group consisting of celluloses, dextrans, and alginates.

42. The method of clause 39 to 41 wherein the gel comprises a cellulose.

43. The method of clause 42 wherein the cellulose is methylcellulose.

44. The method of clause 39 to 43 wherein the gel comprises about 0.25 weight % to about 10 weight % of the methylcellulose.

45. The method of clause 39 to 43 wherein the gel comprises about 0.5 weight % to about 4.0 weight % of the methylcellulose.

46. The method of clause 1 to 45 wherein the hormone is administered with a stabilizer, and wherein the stabilizer is L-methionine.

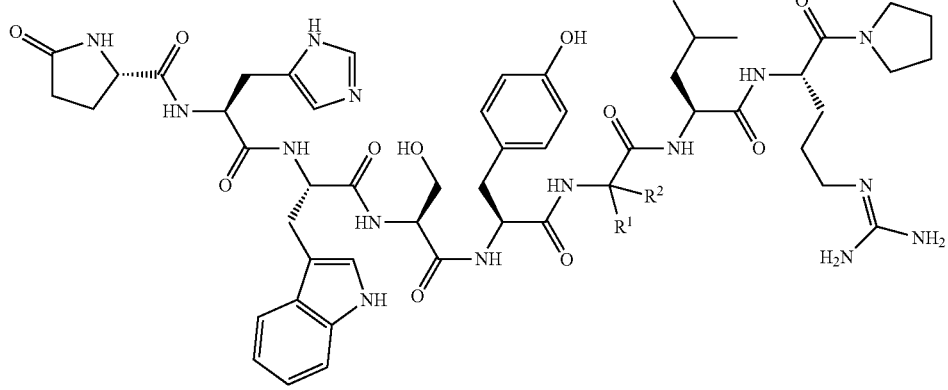

or a solvate, a hydrate, or a pharmaceutically acceptable salt thereof, wherein $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;

X is hydrogen, or X is selected from the group consisting of, alkyl, cycloalkyl, heteroalkyl, optionally substituted alkylene-carboxamide; and HNC(O)NR$^3$R$^4$, where $R^3$ and $R^4$ are in each instance independently selected from the group consisting of hydrogen, alkyl, heteroalkyl and haloalkyl.

35. The method of clause 34 wherein $R^1$ is methylene-heteroaryl, and where heteroaryl is selected from the group consisting of pyridyl, thiazolyl, pyridazolyl, pyrimidinyl, quinolinyl, pyrazolyl, imidazolyl, pyrrolyl, indolyl, benzopyrazolyl, and benzimidazolyl; and $R^2$ is hydrogen or methyl.

36. The method of clause 34 to 35 wherein X is CH$_2$C(O)NH$_2$.

47. A kit comprising a dose of a hormone selected from the group consisting of a gonadotropin releasing hormone, a luteinizing hormone, a human chorionic gonadotropin, and combinations thereof, and instructions for use wherein the hormone is in a composition comprising a gel and the composition has a pH of about 5 to about 6 is described.

48. The kit of clause 47 wherein the instructions indicate that the hormone should be administered to a swine on about the fourth day after weaning and that the swine should be inseminated one time about 15 to about 24 hours after administration of the hormone.

49. The kit of clause 47 to 48 wherein the instructions indicate that the insemination should be an artificial insemination.

50. The kit of clause 47 to 49 wherein the instructions indicate that the insemination should be through natural breeding.

51. The kit of clause 47 to 50 wherein the kit further comprises a deposition catheter, an applicator for manual administration, or a syringe.

52. The kit of clause 47 to 51 wherein the instructions indicate the swine should be inseminated about 15 to about 18 hours after administration of the hormone.

53. The kit of clause 47 to 51 wherein the instructions indicate the swine should be inseminated about 16 to about 24 hours after administration of the hormone.

54. The kit of clause 47 to 51 wherein the instructions indicate the swine should be inseminated about 18 to about 22 hours after administration of the hormone.

55. The kit of clause 47 to 54 wherein the instructions indicate that the swine should be inseminated about 18 hours after administration of the hormone.

56. The kit of clause 47 to 55 wherein the instructions indicate that the hormone should be administered intravaginally.

57. The kit of clause 47 to 56 wherein the instructions indicate that the hormone should be administered in an effective amount of about 10 μg to about 1000 μg.

58. The kit of clause 47 to 56 wherein the instructions indicate that the hormone should be administered in an effective amount of about 10 μg to about 500 μg.

59. The kit of clause 47 to 58 wherein the instructions indicate that the hormone should be administered into the anterior vagina.

60. The kit of clause 47 to 59 wherein the hormone is a gonadotropin releasing hormone receptor agonist.

61. The kit of clause 47 to 60 wherein the hormone is a luteinizing hormone receptor agonist.

62. The kit of clause 47 to 61 wherein the hormone is a human chorionic gonadotropin receptor agonist.

63. The kit of clause 47 to 62 wherein the hormone is triptorelin.

64. The kit of clause 47 to 63 wherein the hormone is a triptorelin salt.

65. The kit of clause 47 to 64 wherein the gonadotropin releasing hormone has the formula pGlu-His-Trp-Ser-Tyr-Gly-Leu-Arg-Pro-GlyNH$_2$.

66. The kit of clause 47 to 65 wherein the gonadotropin releasing hormone receptor agonist has the formula heteroaryl, arylalkyl, and heteroarylalkyl, each of which is optionally substituted, or $R^1$ and $R^2$ and the attached carbon form a carbocycle or heterocycle;

X is hydrogen, or X is selected from the group consisting of, alkyl, cycloalkyl, heteroalkyl, optionally substituted alkylene-carboxamide; and HNC(O)NR$^3$R$^4$, where $R^3$ and $R^4$ are in each instance independently selected from the group consisting of hydrogen, alkyl, heteroalkyl and haloalkyl.

67. The kit of clause 66 wherein $R^1$ is methylene-heteroaryl, and where heteroaryl is selected from the group consisting of pyridyl, thiazolyl, pyridazolyl, pyrimidinyl, quinolinyl, pyrazolyl, imidazolyl, pyrrolyl, indolyl, benzopyrazolyl, and benzimidazolyl; and $R^2$ is hydrogen or methyl.

68. The kit of clause 66 to 67 wherein X is CH$_2$C(O)NH$_2$.

69. The kit of clause 47 to 68 wherein the hormone is synthetic.

70. The kit of clause 47 to 69 wherein the hormone is in acetate form.

71. The kit of clause 47 to 70 wherein the gel comprises a saccharide.

72. The kit of clause 47 to 71 wherein the gel comprises a polysaccharide.

73. The kit of clause 72 wherein the polysaccharide is selected from the group consisting of celluloses, dextrans and alginates.

74. The kit of clause 47 to 73 wherein the gel comprises a cellulose.

75. The kit of clause 74 wherein the cellulose is methylcellulose.

76. The kit of clause 47 to 75 wherein the gel comprises about 0.25 weight % to about 10 weight % of the methylcellulose.

77. The kit of clause 47 to 75 wherein the gel comprises about 0.5 weight % to about 4.0 weight % of the methylcellulose.

78. The kit of clause 47 to 77 further comprising a stabilizer wherein the stabilizer is L-methionine.

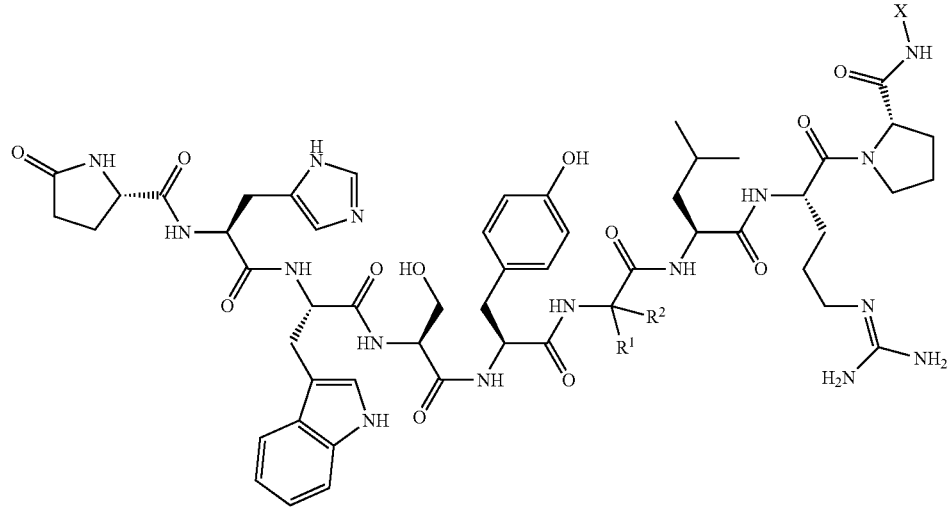

or a solvate, a hydrate, or a pharmaceutically acceptable salt thereof, wherein $R^1$ and $R^2$ are independently in each instance hydrogen, or are independently selected from the group consisting of alkyl, heteroalkyl, cycloalkyl, heterocycloalkyl, haloalkyl, aryl, 79. A composition comprising a gonadotropin releasing hormone receptor agonist and a gel wherein the composition has a pH of about 5.0 to about 6.0 is described.

80. The composition of clause 79 further comprising a preservative.

81. The composition of clause 79 to 80 wherein the preservative is selected from the group consisting of methylparaben and propylparaben.

82. The composition of clause 79 to 81 further comprising a stabilizer.

83. The composition of clause 82 wherein the stabilizer is an L-amino acid.

84. The composition of clause 82 to 83 wherein the stabilizer is L-methionine.

85. The composition of clause 79 to 84 wherein the gel comprises a polysaccharide.

86. The composition of clause 85 wherein the polysaccharide is selected from the group consisting of celluloses, dextrans and alginates.

87. The composition of clause 79 to 86 wherein the gel comprises a cellulose.

88. The composition of clause 87 wherein the cellulose is methylcellulose.

89. The composition of clause 79 to 88 wherein the gel comprises about 0.25 weight % to about 10 weight % of the methylcellulose.

90. The composition of clause 79 to 88 wherein the gel comprises about 0.5 weight % to about 4.0 weight % of the methylcellulose.

91. The composition of clause 79 to 90 further comprising a tonicity agent.

92. The composition of clause 79 to 91 wherein the agonist is triptorelin.

93. The composition of clause 79 to 92 in combination with instructions for use.

94. The composition of clause 93 wherein the instructions in combination with the composition indicate that a swine should be administered the agonist and that the swine should be inseminated one time about 15 to about 24 hours after administration of the agonist.

95. The composition of clause 93 wherein the instructions in combination with the composition indicate that a swine should be administered the agonist and that the swine should be inseminated one time about 16 to about 22 hours after administration of the agonist.

96. The composition of clause 93 wherein the instructions in combination with the composition indicate that a swine should be administered the agonist and that the swine should be inseminated one time about 18 to about 22 hours after administration of the agonist.

97. The composition of clause 93 to 96 wherein the instructions indicate that the swine should be inseminated one time about 18 to about 22 hours after administration of the agonist.

98. The composition of clause 79 to 97 wherein the gonadotropin releasing hormone receptor agonist is gonadotropin releasing hormone, and wherein the gonadotropin releasing hormone has the formula pGlu-His-Trp-Ser-Tyr-Gly-Leu-Arg-Pro-GlyNH$_2$.

99. The composition of clause 79 to 98 wherein the gonadotropin releasing hormone receptor agonist has the formula

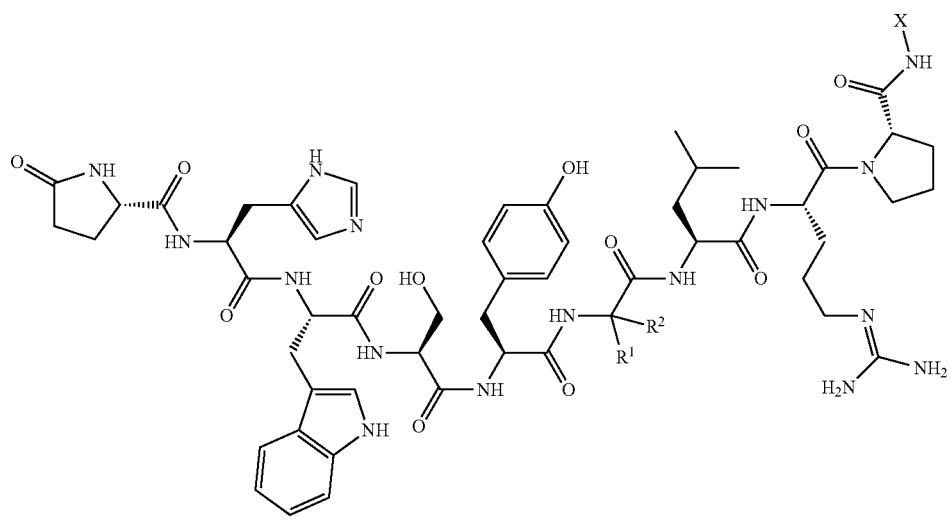

or a solvate, a hydrate, or a pharmaceutically acceptable salt thereof, wherein $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;

X is hydrogen, or X is selected from the group consisting of, alkyl, cycloalkyl, heteroalkyl, optionally substituted alkylene-carboxamide; and HNC(O)NR$^3$R$^4$, where $R^3$ and $R^4$ are in each instance independently selected from the group consisting of hydrogen, alkyl, heteroalkyl and haloalkyl.

100. The composition of clause 99 wherein $R^1$ is methylene-heteroaryl, and where heteroaryl is selected from the group consisting of pyridyl, thiazolyl, pyridazolyl, pyrimidinyl, quinolinyl, pyrazolyl, imidazolyl, pyrrolyl, indolyl, benzopyrazolyl, and benzimidazolyl; and $R^2$ is hydrogen or methyl.

101. The composition of clause 99 to 100 wherein X is CH$_2$C(O)NH$_2$.

102. The composition of clause 79 to 101 wherein the gonadotropin releasing hormone receptor agonist is in an effective amount of about 10 μg to about 1000 μg.

103. The composition of clause 79 to 101 wherein the gonadotropin releasing hormone receptor agonist is in an effective amount of about 10 μg to about 500 μg.

104. The composition of clause 79 to 103 comprising methylparaben, propylparaben, sodium chloride, sodium citrate, L-methionine, citric acid, triptorelin, and methylcellulose.

105. The composition of clause 79 to 104 wherein the composition comprises methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methylcellulose in an amount of about 1.2% weight per volume.

DETAILED DESCRIPTION OF THE ILLUSTRATIVE EMBODIMENTS

Figure 1:
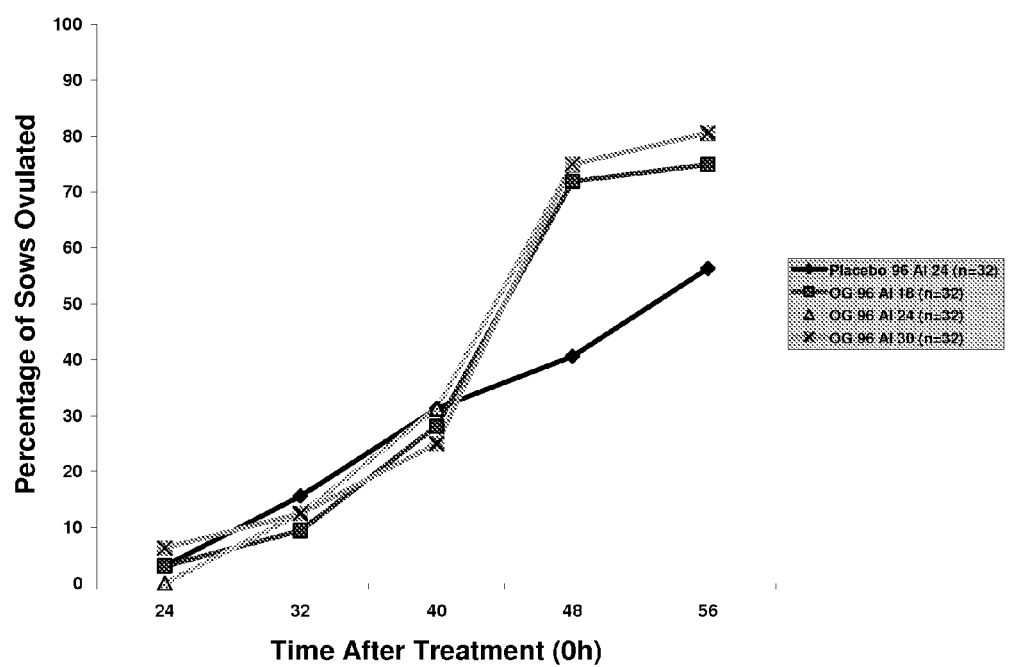
FIG. 1. shows the percentage of sows ovulating following treatments (O-hour) given at 96+/−2 hr post-weaning.

In one embodiment, a method of synchronizing the time of insemination in a swine without heat detection is described. The method comprises the step of administering to the swine, on the fourth day after weaning, a dose of a hormone selected from the group consisting of a gonadotropin releasing hormone, a luteinizing hormone, a human chorionic gonadotropin, and combinations thereof, wherein the swine is inseminated only one time about 15 to about 24 hours after administration of the hormone and wherein there is no heat detection.

In one embodiment, a kit comprising a dose of a hormone selected from the group consisting of, for example, a gonadotropin releasing hormone, a luteinizing hormone, a human chorionic gonadotropin, and combinations thereof is described. In another embodiment, the kit further comprises instructions for use. In yet another embodiment, the hormone is in a composition comprising a gel as herein described. The composition typically has a pH of about 5 to about 6, but the pH may range from about 4 to about 9.

In one embodiment, a composition comprising a gonadotropin releasing hormone receptor agonist is described. In another embodiment, the composition further comprising a gel is described. The composition typically has a pH of about 5 to about 6, but the pH may range from about 4 to about 9.

All of the illustrative embodiments, modifications, and alternative forms described below may be applied to the embodiments described in the preceding paragraphs of this Detailed Description section and to the embodiments described in the Summary of Invention.

The method for synchronizing the time of insemination in a swine without heat detection includes the step of administering to the swine, a dose of a hormone, for example, a gonadotropin releasing hormone, a luteinizing hormone, a human chorionic gonadotropin, derivatives or analogs of gonadotropin-releasing hormone, luteinizing hormone, or human chorionic gonadotropin, or combinations thereof. In accordance with one embodiment, the hormone is administered to a swine. Any porcine species, e.g., gilts (i.e., female pigs prior to first mating), including pubertal gilts, and sows, including postpartum sows, or any other type of swine, may be used in the methods and may be administered the compositions herein described.

Illustratively, swine are weaned on day 0 as herein described. Animals typically receive a single dose of the hormone on day 4 post-weaning (i.e., the fourth day after weaning). Animals receiving treatment are typically inseminated a single time at 15 hours (or 15 hours±2 hr), 16 hours (or 16 hours±2 hr), 17 hours (or 17 hours±2 hr), 18 hours (or 18 hours±2 hr), 19 hours (or 19 hours±2 hr), 20 hours (or 20 hours±2 hr), 21 hours (or 21 hours±2 hr), 22 hours (or 22 hours±2 hr), 23 hours (or 23 hours±2 hr), 24 hours (or 24 hours±2 hr), 27 hours (or 27 hours±2 hr), or 30 hours (or 30 hours±2 hr) post hormone administration.

Breeding of the animal may be by any means of artificial insemination (AI), or through natural breeding. In any embodiment described herein, a second breeding or subsequent breedings may be performed. In yet another embodiment, the swine is inseminated only one time. In another illustrative aspect, there is no heat detection. In another aspect, there is no heat detection between hormone administration and 48 hours after ovulation.

In any embodiment described herein, the hormone is administered, for example, on the fourth day after weaning, i.e. about 96 hours after weaning. In various illustrative embodiments, the hormone can be administered, for example, about 80, about 82, about 84, about 86, about 88, about 90, about 91, about 92, about 93, about 94, about 95, about 96, about 97, about 98, about 99, about 100, about 102, about 104, or about 108 hours after weaning. More typically, the hormone is administered from about 94 to about 98 hours after weaning, i.e., about 94, about 95, about 96, about 97 or about 98 hours after weaning. In another embodiment, the hormone is administered from about 92 to about 106 hours after weaning.

In any embodiment described herein, the swine is inseminated one time, for example, about 15 to about 24 hours after administration of the hormone. In various further illustrative embodiments, the swine is inseminated about 15 to about 18 hours after administration of the hormone, about 13 to about 18 hours, about 15 to about 20 hours, or about 13 to about 20 hours after administration of the hormone. In other illustrative aspects, the swine is inseminated about 13 hours, about 14 hours, about 15 hours, about 16 hours, about 17 hours, about 18 hours, about 19 hours, about 20 hours, about 21 hours, about 22 hours, about 23 hours, or about 24 hours after administration of the hormone. Illustratively, the swine is inseminated about 15 hours, about 18 hours, about 20 hours, about 22 hours, or about 24 hours after administration of the hormone.

In any embodiment described herein, the pregnancy rate of the swine can be increased relative to a swine to which no hormone is administered (e.g., to which a placebo is administered). For example, the pregnancy rate in hormone-treated animals can be about 75% to about 90%. In another embodiment, the litter size of the swine can be increased relative to a swine to which no hormone is administered (e.g., to which a placebo is administered). For example, the typical litter size in hormone-treated animals can be about 20 to about 24 fetuses per pregnancy. In other embodiments, the litter size in hormone-treated animals can be about 14 to about 18, about 14 to about 24, or about 14 to about 20 fetuses per pregnancy. In yet another embodiment, the percentage of swine ovulating by about 48 hours after administration of the hormone can be increased relative to swine to which no hormone is administered (e.g., to which a placebo is administered). For example, the percentage of animals that ovulate by about 48 hours after administration of the hormone can be about 65% to about 85%.

In further embodiments described herein, the total number of healthy fetuses can be increased relative to a swine to which no hormone is administered. For example, the number of healthy fetuses for hormone-treated animals can be about 9 to about 18, about 9 to about 16, about 9 to about 14, or about 9 to about 12. In further embodiments described herein, the percent farrowed for hormone-treated animals can be increased when compared to swine to which no hormone is administered. For example, the percentage farrowed for hormone-treated animals can be about 76% to about 90%, about 76% to about 85%, or about 76% to about 80%. In further embodiments described herein, the total number of piglets born to hormone-treated animals can be increased relative to a swine to which no hormone is administered. For example, the number of piglets born can be about 13 to about 18, about 13 to about 17, about 13 to about 16, about 13 to about 15, or about 13 to about 14. In any embodiment described herein, the pregnancy rate of the swine, the litter size of the swine, the total number of healthy fetuses, the farrowing percent, and the total number of piglets born, for hormone-treated animals, can be similar to that of animals inseminated upon heat detection.

In any embodiment described herein, the total number of piglets born per semen dose can be increased relative to a swine to which no hormone is administered, and the total number of piglets born per semen dose can be increased relative to animals inseminated upon heat detection. For example, the total number of piglets born ser semen dose can be about 6, about 7, about 8, about 9, about 10, about 11, about 12, about 14, about 16, about 18, or about 20. In any embodiment described herein, the piglet index (pigs born alive/100 sows allotted) can be increased relative to a swine to which no hormone is administered, and the piglet index can be increased relative to animals inseminated upon heat detection.

In any embodiment described herein, compositions for synchronizing the time of insemination in a swine without heat detection comprise: a) a hormone; and b) a pharmaceutically acceptable pH buffering agent to provide a pH in the range of about pH 4 to about pH 9. The pH of the composition herein described can range from about 4 to about 9. In other embodiments, the pH can range from about 4 to about 8, from about 4 to about 7, from about 4.5 to about 6.5, about 4.5 to about 6, or from about 5 to about 6.

Further, the hormone compositions can be produced, in accordance with the dosage form, through a routine method by appropriately mixing with, diluting with, or dissolving in an additive such as various excipients, disintegrants, binders, salts, lubricants, local anesthetics (e.g., lidocaine), diluents, preservatives, chelating agents, buffers, tonicity agents, antiseptic agents, wetting agents, emulsifiers, dispersants, stabilizers, a solution adjuvant, or combinations thereof.

Illustratively, the compositions comprising the hormone can be in the form of a gel and the composition can have, for example, a viscosity of about 10 (centipoise) cP to about 300,000 cP. In various illustrative embodiments, the viscosity of the composition can be about 100 cP to about 100,000 cP, about 250 cP to about 400 cP, about 300 cP to about 400 cP, about 500 cP to about 100,000 cP, about 700 cP to about 100,000 cP, about 200 cP to about 20,000 cP, about 200 cP to about 10,000 cP, about 200 cP to about 5,000 cP, about 200 to about 1,000 cP, about 200 cP to about 600 cP, about 100 cP to about 600 cP, about 100 cP to about 500 cP, about 200 cP to about 500 cP, about 200 cP to about 450 cP, or about 100,000 cP to about 250,000 cP. In accordance with various embodiments herein described, the viscosity of the composition can be about 200 cP, about 250 cP, about 300 cP, about 400 cP, about 500 cP, about 1,000 cP, about 15,000 cP, about 20,000 cP, about 30,000 cP, about 40,000 cP, about 50,000 cP, about 75,000 cP, about 100,000 cP, about 200,000 cP, or about 300,000 cP. The viscosity of a solution can be measured using a viscometer, such as a rheometer, based on techniques well-known in the art.

Typically, the gels as described herein comprise about 0.001 to about 3.0% weight/weight (w/w) of a hormone or a salt thereof, more typically about 0.5-5.0% (w/w) or about 0.1-5.0% (w/w) of a hormone or a salt thereof, a preservative, a gel (i.e., a viscosity-modifying agent), a buffer to maintain a pH between about 5 to about 6, and a tonicity agent to maintain a tonicity between about 200 to about 400 mOsm/kG.

In accordance with any embodiment described herein, the composition is sufficiently viscous that the composition stays adhered to the target tissue for a sufficient time to deliver an effective amount of the hormone. The typical viscosity will depend on factors such as, for example, the rate of penetration of the hormone and the quantity of the hormone that is applied. Suitable viscosity modulating agents include but are not limited to, ionic and non-ionic water soluble polymers; crosslinked acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof.

The viscosity modulating agent may be in the form of a gel, paste, cream, ointment, and the like. In one embodiment, the composition comprises a hormone and a gel, as a viscosity modifying agent, and the hormone is administered in the composition comprising the gel. In one embodiment, the gel is a hydrogel, a lipogel, or a viscous sol. In another embodiment, the gel is a hydrogel. The gel may be prepared using any method known in the art, for example, such as those methods described in U.S. Pat. Nos. 6,908,623 and 7,456,207, incorporated herein by reference.

In any embodiment described herein, the gel (i.e., a viscosity modifying agent) comprises a polysaccharide. In accordance with the methods and compositions herein described, the polysaccharide may include, for example, alginates and glucose, such as glycogens, starches (e.g., amylose and amylopectin), celluloses, and dextrans. The polysaccharide can be, for example, a methyl, ethyl, or propyl cellulose ester, ether, hydroxy-ether, hydroxy-alkyl, or hydroxy-ester. To achieve the desired viscosity, a sufficient amount of one or more polysaccharides may be used. Typically, about 0.25 to about 10 weight % polysaccharide (based on the total weight of the composition) is desirable. In another embodiment, the weight % of the polysaccharide is about 0.25 weight % to about 3.0 weight %, about 1.0 weight % to about 7 weight %, about 1.0 weight % to about 4.0 weight %, or about 1.0 weight % to about 2.0 weight %. In other embodiments, the weight % of the polysaccharide is about 0.1%, about 0.5%, about 0.75%, about 0.8%, about 0.9%, about 1.0%, about 1.1%, about 1.2%, about 1.4%, about 1.8%, about 2.0%, about 5%, about 8%, or about 10% (all in weight/weight). To increase the viscosity of the composition, the polysaccharide may be used in conjunction with one or more non-polysaccharide viscosifiers known in the art. Examples of possible non-polysaccharide viscosifiers that could be used in conjunction with one or more polysaccharides include xanthan gum, alginic acids and salts thereof, magnesium aluminum silicate, dextrins, sucrose and derivatives thereof, and mixtures thereof. The amount of non-polysaccharide viscosifier, if present, can be about 0.1 weight % to about 10 weight %, depending on the desired viscosity.

In any embodiment described herein, the gel comprises a cellulose. Illustrative embodiments of the cellulose, as herein described, include methylcellulose, ethylcellulose, hydroxypropyl cellulose, carbomethyl cellulose, hydroxypropyl methyl cellulose, and hydroxyethyl methyl cellulose. The cellulose can be a cellulose derivative, preferably a non-ionic cellulose ester, ether, hydroxy-ether, or hydroxy-ester, or a non-ionic starch derivative. Typically, about 0.25 weight % to about 10 weight % of the cellulose (based on the total weight of the composition) is desirable. In another embodiment, the weight % of the cellulose is about 0.25 weight % to about 3.0 weight %, about 0.5 weight % to about 3.0 weight %, about 0.5 weight % to about 4.0 weight %, about 1.0 weight % to about 7 weight %, about 1.0 weight % to about 4.0 weight %, or about 1.0 weight % to about 2.0 weight %. In other embodiments, the weight % of the cellulose is about 0.1%, about 0.5%, about 0.75%, about 0.8%, about 0.9%, about 1.0%, about 1.1%, about 1.2%, about 1.4%, about 1.8%, about 2.0%, about 5%, about 8%, or about 10% (all in weight/weight). If a uniform gel is desired, dispersing agents such as alcohol, sorbitol, or glycerin can be added, or the gelling agent can be dispersed by tituration, mechanical mixing, or stirring, or combinations thereof.

Acceptable stabilizers for use in the described methods and compositions include, an L-amino acid and an L-methionine. In other embodiments, stabilizers that can be used include, but are not limited to, polysaccharides such as acacia, agar, alginic acid, guar gum and tragacanth, gelatin and synthetic and semi-synthetic polymers such as carbomer resins, cellulose ethers, and carboxymethyl chitin. The stabilizer is generally in an amount of about 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume). In one embodiment, in the presence of a stabilizer as herein described, the shelf life of the composition can be at least 12 months, at least 18 months, or at least 24 months. In another embodiment, the composition can be stored at temperatures ranging from about 2° C. to about 8° C. Inert carriers can also be included such as lactose, starch, dextrin, dicalcium phosphate, and calcium sulfate. In one embodiment including a stabilizer, the composition is chemically stable and remains at least 99% pure, at least 99.5% pure, or at least 99.7% pure, for at least three months.

The tonicity agent can be non-ionic or ionic. Illustratively, acceptable tonicity agents for use in the described methods and compositions include, for example, ionic agents such as sodium chloride, potassium chloride, or a balanced salt solution. In accordance with one embodiment, the tonicity agent is present in an amount to achieve a tonicity between about 200-400 mOsm/kG, about 220-380 mOsm/kG, or about 250-340 mOsm/kG. Non-ionic tonicity agents include diols, such as glycerol, mannitol, erythritol, polyethylene glycol, propylene glycol; and sugars such as sucrose and dextrose. The tonicity agent is generally in an amount of about 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 0.5 to about 2.0%, about 0.6 to about 2.0%, about 0.5 to about 1.8%, about 0.6 to about 1.8%, about 1.0 to about 5.0%, about 1.0 to about 10%, or about 1.0 to about 20% (all in weight/volume).

In any embodiment described herein, the pH buffering agents for use in the compositions and methods herein described are those agents known to the skilled artisan to be pH buffering agents or compositions and include, for example, acetate, borate, carbonate, citrate, and phosphate buffers, as well as various biological buffers, for example, TAPS, Bicine, Tris, Tricine, HEPES, TES, MOPS, PIPES, Cacodylate, and MES. Other pH buffering agents include hydrochloric acid, sodium hydroxide, magnesium oxide, monopotassium phosphate, bicarbonate, ammonia, carbonic acid, sodium citrate, citric acid, acetic acid, disodium hydrogen phosphate, borax, boric acid, and the like. The buffering agent is generally in an amount of about 0.01 to about 10%, about 0.02 to about 10%, about 0.02 to about 5%, about 0.02 to about 2.0%, about 0.02 to about 1.0%, about 0.02 to about 0.5%, about 0.05 to about 10.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume).

The buffering agent used in the formulations herein described can be used at any concentration needed to obtain the desired pH range. For example, the buffering agent can be used at a concentration of about 0.001M to about 1M, about 0.001M to about 2M, about 0.001M to about 5M, about 0.05M to about 0.1M, about 0.05M to about 0.2M, about 0.05M to about 1M, 0.05M to about 2M, about 0.05 to about 5M, about 0.1M to about 1M, about 0.1M to about 2M, about 0.1M to about 5M. Any amount of buffering agent needed to obtain the desired pH range can be used in the formulations described herein. Typically, the pharmaceutically acceptable pH buffering agent can be used to provide a pH in the range of about pH 4 to about pH 9. The pH of the composition herein described can range from about 3 to about 10, or about 4 to about 9. In any embodiment described herein, the pH can range from about 4 to about 8, from about 4 to about 7, from about 4.5 to about 6.5, about 4.5 to about 6, from about 5 to about 6, about 5 to about 5.5, about 4 to about 6, or about 4.5 to about 5.5.

In any embodiment described herein, the composition herein described comprises one or more pharmaceutically acceptable preservatives. As used herein, the term "preservative" includes an agent or a combination of agents that aids in stabilizing the composition, inhibiting microbial growth, or both. Examples of suitable preservatives include parabens (e.g., methyl, ethyl, propyl, and butyl esters of parahydroxybenzoic acid), propyl gallate, sorbic acid and its sodium and potassium salts, propionic acid and its calcium and sodium salts, "Dioxin" (6-acetoxy-2,4-dimethyl-m-dioxane), "Bronopol" (2-bromo-2-nitropropane-1,3-diol) and salicylanilides such as disbromosalicylanilide, tribromosalicylamilides, "Cinaryl" 100 and 200 or "Dowicil" 100 and 200 (Cis isomer of 1-(3-chloroallyl-3,5,7-triaza-1-azanidadamantane chloride), hexachlorophene, sodium benzoate, citric acid, ethylene diaminetetraacetic acid and its alkali metal and alkaline earth metal salts, butyl hydroxyanisol, butyl hydroxytoluene, phenolic compounds such as chloro- and bromocresols and chloro- and bromo-oxylenols, quaternary ammonium compounds like benzalkonium chloride, aromatic alcohols such as phenylethyl alcohol, benzyl alcohol, etc., chlorobutanol, quinoline derivatives such as iodochlorohydroxyquinolin, and the like. The total amount of preservative, when present, is about 0.005 weight % to about 2 weight %, about 0.001 weight % to 1.0 weight %, about 0.005 weight % to about 0.25 weight %, or about 0.05 weight % to about 0.2 weight %, typically about 0.01 weight % to about 0.1 weight % (all in weight/weight).

In any embodiment described herein, the pharmaceutical composition contains a chelating agent, such as those known to those skilled in the art, for example, ethylenediamine tetraacetate (EDTA), diethylenetriaminepentaacetic acid (DTPA), and N,N-bis(carboxymethyl)glycine (NTA), or salts thereof. The composition can contain about 0.003 weight % to about 1.0 weight %, about 0.02 weight % to about 0.2 weight %, about 0.01 weight % to about 1.0 weight %, or about 0.02 weight % to about 0.5 weight % (all in weight/volume) of the chelating agent.

In any embodiment described herein, antimicrobial agents can be included in the compositions described herein. Such agents may include, but are not limited to 5-chloro-2-(2,4-dichlorophenoxy)-phenol, 8-hydroxyquinoline, copper II compounds, phthalic acid, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride, octenidine, iodine, sulfonamides, bisbiguanides, phenolics, delmopinol, octapinol, and other piperidino derivatives, and nicin preparations, any suitable antibiotics such as augmentin, amoxicillin, tetracycline, doxycycline, minocycline, metronidazole, neomycin, kanamycin, and clindamycin, and any salts of any of these compounds where applicable, and any combinations of these compounds. In yet another embodiment, anti-fungal compounds can be included, alone or in combination with any of the above-described antimicrobials. Anti-fungals agents that are suitable for use in the compositions described herein include, but are not limited to, nystatin, miconazole, econazole nitrate, clotrimazole, and flucytosine. The antimicrobial or anti-fungal agents can be added to the formulations herein described in an amount of about 0.01 to about 10%, about 0.01 to about 5%, about 0.01 to about 2.0%, about 0.01 to about 1.0%, about 0.01 to about 0.5%, about 0.01 to about 0.2%, 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume).

In any embodiment described herein, antioxidants can also be added. For example, antioxidants used herein can include beta-carotene, vitamin E, vitamin C, vitamin A, tocopherol, butylated hydroxytoluene, butylated hydroxyanisole, tertiary-butylhydroquinone, propyl gallate, ascorbic acid, sodium metabisulfite, uric acid, carotenoids, flavonoids, melatonin, and ethoxyquin. The antioxidants can be added to the formulations herein described in an amount of about 0.01 to about 10%, about 0.01 to about 5%, about 0.01 to about 2.0%, about 0.01 to about 1.0%, about 0.01 to about 0.5%, about 0.01 to about 0.2%, 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume).

As described herein, the composition contains a hormone selected from the group consisting of, for example, gonadotropin releasing hormone, luteinizing hormone, human chorionic gonadotropin, derivatives and analogs thereof, and combinations thereof, in an amount effective to synchronize the time of insemination in a swine without heat detection when used in the method described herein. Additional examples of acceptable hormones for use in the methods and compositions described herein include, prostaglandins, progestogens, progesterones, angrogens, testosterones, estrogens, estradiols, gonadotropins, derivatives and analogs thereof, combinations thereof, and the like. The hormone can be in acetate form. Further, the hormone can be a gonadotropin-releasing hormone, luteinizing hormone, or human chorionic gonadotropin agonist or a gonadotropin-releasing hormone, luteinizing hormone, or human chorionic gonadotropin antagonist. As used herein, "gonadotropin-releasing hormone" refers to any gonadotropin releasing hormone, including gonadotropin releasing hormone analogs and derivatives, and gonadotropin releasing hormone agonists and antagonists. In one embodiment, the gonadotropin releasing hormone can be synthetic. In another embodiment, the gonadotropin-releasing hormone can be GnRH (pGlu-His-Trp-Ser-Tyr-Gly-Leu-Arg-Pro-GlyNH$_2$)(see, for example, U.S. Pat. No. 5,688,506, incorporated herein by reference) or triptorelin. As used herein, "luteinizing hormone" refers to any luteinizing hormone, including luteinizing hormone analogs and derivatives, and luteinizing hormone agonists and antagonists. In one embodiment, the luteinizing hormone can be synthetic. In another embodiment, the luteinizing hormone can be LH (see, for example, U.S. Pat. No. 5,444,167, incorporated herein by reference). As used herein, "human chorionic gonadotropin" refers to any human chorionic gonadotropin, including human chorionic gonadotropin analogs and derivatives, and human chorionic gonadotropin agonists and antagonists. In one embodiment, the human chorionic gonadotropin can be synthetic. In another embodiment, the human chorionic gonadotropin can be hCG (see, for example, U.S. Pat. Nos. 6,469,139, 4,400,316, and 4,804,626, incorporated herein by reference).

Examples of gonadotropin releasing hormone agonists for use herein include, but are not limited to, leuprolide, nafarelin, buserelin, [DAla$^6$, des Gly-NH$_2$$^{10}$]GnRH, [DLys$^6$] GnRH, [DAla$^6$]GnRH, [2-Me-Ala$^6$]GnRH, [D-α-aminobutyroyl$^6$, des-GlyNH$_2$$^{10}$]GnRH, triptorelin, lutrelin, goserelin, deslorelin, and histrelin. Generally, gonadotropin releasing hormone agonists are modeled after the natural gonadotropin releasing hormone decapeptide with specific amino acid substitutions typically at positions 6 and 10. Triptorelin is an example of a gonadotropin releasing hormone agonist with only a single substitution at position 6.

Examples of gonadotropin releasing hormone antagonists include Antide (a decapeptide represented by the formula D-Ac-D-2-Nal$^1$-DpClPhe$^2$-D-3-Pal$^3$-Ser4-NiLys$^5$-D-NicLys$^6$-Leu$^7$-ILys$^8$-Pro$^9$-D-Ala$^{10}$), [Ac-D4ClPhe$^1$, D4ClPhe$^2$, DTrp$^3$, DArg$^6$, DAla$^{10}$]GnRH, [Ac-4ClDPhe$^2$, D$_3$Pal$^3$, Arg$^5$, D$_2$Nal$^6$, DAla$^{10}$]GnRH, [Ac-D2-Na$^1$l, 4ClDPhe$^2$, DTrp$^3$, DArg$^6$, DAla$^{10}$]GnRH, [Ac-D2 Nal$^1$, 4FDPhe$^2$, DTrp$^3$, DArg$^6$]GnRH, [Ac-D2Nal$^1$, 4ClDPhe2, DTrp$^3$, DhArg(Et$_2$)$^6$, DAla$^{10}$]GnRH, and [Ac—Na$^1$l, DME4ClPhe$^2$, DPal$^3$, Ser$^4$, Tyr$^5$, DArg$^6$, Le$^7$, ILys$^8$, Pro$^9$, DAla$^{10}$]GnRH.

In any embodiment described herein, the use of a gonadotropin releasing hormone agonist of formula

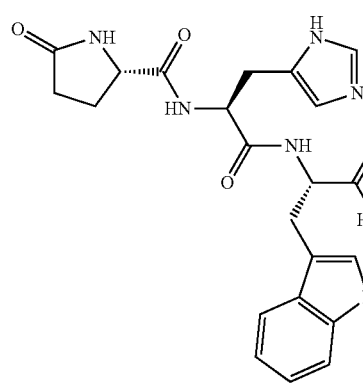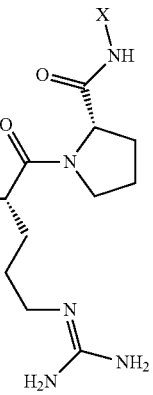

or a solvate, a hydrate, or a pharmaceutically acceptable salt thereof is described wherein $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle; and X is hydrogen, or X is selected from the group consisting of, alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

In another embodiment, the above use wherein $R^1$ is methylene-heteroaryl, where heteroaryl is selected from the group consisting of pyridyl, thiazolyl, pyridazolyl, pyrimidinyl, quinolinyl, pyrazolyl, imidazolyl, pyrrolyl, indolyl, benzopyrazolyl, and benzimidazolyl; and $R^2$ is hydrogen or methyl is described.

In yet another embodiment, any one of the previously described uses wherein X is $CH_2C(O)NH_2$ is described.

The gonadotropin releasing hormone agonists and antagonists, and analogs thereof, such as the analogs described in the formula above, used herein can be administered in the form of pharmaceutically acceptable non-toxic salts or complexes. The salts include acid addition salts such as, for example, hydrochloride, hydrobromide, sulfate, phosphate, nitrate, oxalate, fumarate, gluconate, tannate, maleate, acetate, benzoate, succinate, alginate, malate, ascorbate, tartrate and the like. The complexes can be with metals such as for example zinc, barium, calcium, magnesium, aluminum and the like.

The amount of the hormone effective for use in accordance with the methods and compositions described herein depends on many parameters, including the molecular weight of the hormone, its route of administration, and whether it is in its native form. As in described herein an "effective amount" of the hormone is an amount sufficient to synchronize the time of insemination in a swine without heat detection by using the method described herein. The effective amount of the hormone to be administered to a swine can range from about 10 µg to about 2000 µg, about 10 µg to about 1000 µg, about 10 µg to about 500 µg, about 10 µg to about 100 µg, about 10 µg to about 50 µg, about 50 µg to about 2000 µg, about 50 µg to about 1000 µg, about 50 µg to about 500 µg, about 50 µg to about 300 µg, about 50 µg to about 200 µg, about 100 µg to about 200 µg, about 100 µg to about 300 µg, about 100 µg to about 500 µg, about 100 µg to about 1000 µg, about 200 µg to about 2000 µg, or about 0.05 mg to about 50 mg. In various illustrative aspects, the hormone can be administered to a swine at a dose of about 20 µg, about 50 µg, about 75 µg, about 100 µg, about 150 µg, about 180 µg, about 200 µg, about 225 µg, about 250 µg, about 300 µg, about 400 µg, about 500 µg, about 750 µg, about 1000 µg, about 1500 µg, or about 2000 µg of the hormone. The hormone can be administered in one or more doses.

The hormone in the composition described herein can be administered at a concentration of, for example, about 50 µg/mL to about 500 µg/mL, about 50 µg/mL to about 400 µg/mL, about 50 µg/mL to about 300 µg/mL, about 50 µg/mL to about 200 µg/mL, about 50 µg/mL to about 150 µg/mL, about 50 µg/mL to about 250 µg/mL, or about 100 µg/mL. The composition can be administered in various volumes including for example a dosage volume of 1 mL, 2 mL, 3 mL, 4 mL, or 5 mL.

In any embodiment described herein, the hormone is administered in an amount effective to stimulate ovarian follicle ovulation and to synchronize ovulation according to the method described herein. The dose of the hormone can be administered using a method selected from the group consisting of 1) use of a deposition catheter, 2) manual administration, 3) injection, or any other art recognized means for administering a pharmaceutical composition, for example, any other art recognized means for vaginally administering a pharmaceutical composition, such as a composition containing a hormone. In one embodiment, the hormone can be administered to more than one swine.

Examples of methods for effective hormone administration, other than vaginal administration, include parenteral administration to the animal, for example, subcutaneously, intramuscularly, intraperitoneally, intrathecally, or intravenously, or in combination with an acceptable carrier. Suitable means for parenteral administration include needle (including microneedle) injectors, needle-free injectors, and infusion techniques. The parenteral compositions for use in accordance with this invention can be in the form of a reconstitutable lyophilizate comprising one or more doses of the hormone composition. Examples of parenteral dosage forms include aqueous solutions of the composition in well-known acceptable liquid carriers such as liquid alcohols, glycols (e.g., polyethylene glycols), glucose solutions (e.g., 5%), esters, amides, sterile water, buffered saline (including buffers like phosphate or acetate; e.g., isotonic saline).

In any embodiment described herein, the composition can be administered to the animal locally. Examples of local administration methods for use herein include, topical, intravaginal, and intrarectal. Examples of dosage forms for use in this embodiment include creams, ointments, gels, pastes, powders, lotions, transdermal patches, intrauterine devices, vaginal rings, and vaginal tablets. In one illustrative embodiment, the composition is administered into the anterior vagina of the animal. The compounds may also be formulated in vaginal or rectal compositions such as suppositories, e.g., containing conventional suppository bases such as cocoa butter, carbowaxes, polyethylene glycols or other glycerides, all of which melt at body temperature, yet are solidified at room temperature.

The hormone may be administered to the animal by any useful procedures and any effective dose and suitable dosage form can be used, including oral dosage forms known in the art, such as pills, pellets, or capsules, and effective doses can be administered in standard or modified release dosage forms. Modified release dosage formulations include delayed, sustained, pulsed, controlled, targeted, and programmed release formulations.

The compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

In another illustrative aspect of the invention, a kit is provided. The kit comprises a dose or multiple doses of a hormone as described herein. In this embodiment, the kit can further comprise an applicator for manual administration, a deposition catheter, and/or a syringe for application of the hormone composition to an animal. In yet another embodiment, the hormone is in a composition comprising a gel as described herein. In one illustrative embodiment, the kit may comprise the hormone and the gel separately for mixing before administration to the animal. In another embodiment, the kit may comprise the hormone and the gel admixed in a vessel for immediate administration.

In yet another embodiment, the kit contains instructions for use. The instructions may indicate that the insemination should be through natural breeding; the insemination should be through artificial insemination; the swine should be inseminated at about 15 to about 18, about 18 to about 22, or about 15 to about 24 hours after administration of the hormone; or the swine should be inseminated at about 15, about 16, about 17, about 18, about 19, about 20, about 21, about 22, about 23, about 24, or about 30 hours after administration of the hormone. Other suitable kit components include excipients, disintegrants, binders, salts, lubricants, local anesthetics (e.g., lidocaine), diluents, preservatives, chelating agents, buffers, tonicity agents, antiseptic agents, wetting agents, emulsifiers, dispersants, stabilizers, and the like. These components may be available separately or admixed with the hormone and/or gel as necessary. Any of the hormone embodiments and any of the composition embodiments described herein can be used to formulate the kit.

In yet another embodiment, an article of manufacture is provided. The article of manufacture can comprise any of the compositions described herein. The composition can be in a primary container, for example, a glass vial, such as an amber glass vial with a rubber stopper and/or an aluminum tear-off seal. In another embodiment, the primary container can be plastic or aluminum, and the primary container can be sealed. In another embodiment, the primary container may be contained within a secondary container to further protect the composition from light. The secondary container can be, for example, cardboard. Any of these embodiments also apply to the kit embodiments described above, and any of the hormone and composition embodiments described herein can apply to the article of manufacture.

EXAMPLES

Example 1

Study Design and Treatment Groups

Approximately 120 parity one to seven sows (30 sows within each treatment group) were used to obtain ovulation and reproductive tract data. All sows were of the same genotype (PIC C22). Following 16 to 24 days of lactation, sows were blocked by length of lactation and parity and randomly assigned to one of four treatments: 1) a placebo group, receiving a placebo gel at 96±2 hours post-weaning and a single AI 24 hours later, 2) triptorelin gel at 96±2 hours post-weaning and AI 18 to 20 hours later. 3) triptorelin gel at 96±2 hours post-weaning and AI 24 to 26 hours later, and 4) triptorelin gel at 96±2 hours post-weaning and AI 30 to 32 hours later. The placebo formulation was identical to the active formulation but without the hormone being present. All treatments were deposited into the anterior vagina within 2 cm of the cervix. Follicular development and ovulation was monitored via real time ultrasound at 24, 32, 40, 48, and 56 hours after treatment. Thirty (30) days after insemination, all sows were slaughtered and reproductive tracts obtained. Pregnancy rates and embryo survival were determined.

Example 2

Test Substance

The active ingredient was triptorelin (pGlu-His-Trp-Ser-Tyr-D-Trp-Leu-Arg-Pro-Gly-$NH_2$) supplied in the acetate form (molecular weight: 1371.6), from Bachem, Torrance, Calif. (Item H-4075 CGMP grade). Triptorelin gel (200 µg/2 mL), lot 054023833-1, was formulated at Chem Laboratories Ltd (Auckland, New Zealand) in a gel composed of 1.2% Methocel™ Premium A4000 (Dow Chemicals) in sodium citrate, pH 5.5 with methyl and propyl paraben, NaCL, EDTA and L-methionine. Formulation vehicle, lot 054006645-1, was formulated at Chem Laboratories Ltd. and was composed of 1.2% Methocel™ Premium A4000 (Dow Chemicals) in sodium citrate, pH 5.5 with, NaCl and methyl and propyl paraben. Fifty milliliters of triptorelin gel (200 µg triptorelin acetate/mL) or formulation vehicle were packaged in a 50 mL Amber Borosilicate Glass Serum Vials (610206-50) with a Gray Butyl Pharmaceutical Serum Vial Stopper (73828A-SS) with a Standard Aluminum Seal (SAS20NAT). The test substances were stored refrigerated (about 5° C.) and transported in insulated containers with appropriate ice packs.

Example 3

Example Formulations

Example formulations for the composition described in this application are shown in Tables 1 and 2.

TABLE 1

| Ingredient | Function | Weight (% w/v) |
|---|---|---|
| Methylparaben, sodium salt (USNF) | Anti-microbial preservative | 0.0900 |
| Propylparaben, sodium salt (USNF) | Anti-microbial preservative | 0.0100 |
| Sodium chloride, laboratory reagent | Tonicity agent | 0.910 |
| Sodium citrate, dihydrate | Buffering agent | 0.186 |
| L-Methionine, laboratory reagent | Stabilizing agent | 0.100 |
| Citric acid, anhydrous | Buffer | 0.0700 |
| Triptorelin acetate | Active Pharmaceutical Ingredient (API) | 0.0100 |
| Water (USNF) | Dissolving solvent | 98.4 |
| Methylcellulose (A4M Premium) (USP) | Thickening agent | 1.20 |

TABLE 2

| Component | Quality Standard | Function | Amount per 100 mg % w/w |
|---|---|---|---|
| Triptorelin Acetate | In house | Drug Substance | 11.0 mg 0.011%* |
| Purified Water | USP | Solvent | 97.6 g 97.54%* |
| Methylparaben, Sodium Salt** | NF | Preservative | 89.0 mg 0.089%* |
| Propylparaben, Sodium Salt** | NF | Preservative | 10.0 mg 0.010** |
| Sodium Chloride | USP | Tonicity agent | 901 mg 0.901% |
| L-Methionine | USP | Stabilizing agent | 99.0 mg 0.099% |
| Sodium Citrate | USP | Buffering agent | 184 mg 0.184% |
| Citric Acid | USP | Buffering agent | 69.0 mg 0.069%* |
| Methycellulose | USP | Viscosity modifier | 1.1 g 1.10%* |

*Nominal amount
**Tested to compendial standard

Example 4

Estrus Observation

Sows were housed in gestation crates following weaning (Day 0). Boars were housed in separate rooms, and/or at least 12 m away and downwind. To determine onset and duration of estrus, sows were observed for estrus daily (1) from Day 3 until the end of estrus was confirmed, or (2) until Day 6, which ever came first. To elicit signs of estrus, a mature boar was walked slowly in the alley in front of the crates of the sows, exposing each test sow to visual, auditory and olfactory signals from the boar for up to 5 min. In keeping with standard practice at commercial farms, while the boar was near the front of the sow's crate, estrus was tested by an experienced person applying back pressure to the midsection of the sow combined with side rubbing. Estrus was confirmed when a sow stood rigidly to the back pressure, with no vocalization and with some indication of an ear reflex.

Example 5

Administration and Insemination

Triptorelin was administered at 96 hours (±2 hr) post-weaning as a single 2 mL dose deposited approximately 1-2 cm posterior to the cervix with a modified artificial insemination catheter. Weaning of sows occurred between 10 a.m. and noon on Day (0). The timing of the insemination for each group of sows was given as directed in the protocol. Those sows scheduled to be inseminated 18 hours following administration of triptorelin were generally inseminated between 6:00 a.m. and 8:00 a.m. the following day, those sows scheduled to be inseminated 24 hours following administration of triptorelin were generally inseminated between noon and 2:00 p.m. the following day and those sows scheduled to be inseminated 30 hours following administration of triptorelin were generally inseminated between 6:00 p.m. and 8:00 p.m. the following day. The single insemination for each sow was performed as they were normally done at the farm.

Example 6

Ovulation and Estrus Detection

All sows were observed for ovulation by transrectal ultrasonography. Ultrasonography was performed at 24 hr (±1.5 hour) after treatment on Day 5 and again at 8:00 p.m. (±1.5 hour) on Day 5. On Day 6 transrectal ultrasonography was performed at 4:00 a.m. (±1 hour), noon (±1 hr) and 8:00 p.m. (±1 hr) until ovulation was complete or until the 8:00 p.m. ultrasonography on Day 6 (the 56 hour mark from the animals treated at 96 hours post-weaning) whichever came first. An Aloka 500 ultrasound machine was used for this purpose, with a 7.5 MHz linear array transducer attached to a fixed-angle PVC stabilizing rod to facilitate insertion into the rectum. The transducer and PVC rod were coated with a gynecological lubricant and gently inserted into the rectum until the ovaries could be visualized, one at a time. The diameters of the three largest follicles were to be recorded (to the nearest 0.1 mm) at each scanning. A sow was declared to have ovulated when the number of large follicles ($\geq 6.5$ mm) fell to less than 3.

On Day 5 post-weaning, the average size of the largest follicle was 7.3 mm and was not influenced by treatment. Estrus expression within 7 days of weaning averaged 79% and did not differ significantly among treatments. There was also no effect of treatment on the interval from weaning to estrus (average 112 hours).

The percentage of sows that had ovulated was not significantly affected by treatment, at 24 hours, 32 hours or 40 hours following treatment (see Table 3 and FIG. 1). However, the percentage of sows ovulating by 48 hours after treatment was increased (p=0.0054) in all triptorelin treated groups [74.0% (AI at 18 hours), 77.0% (AI at 24 hours), and 76.8% (AI at 30 hours)] compared to vehicle treated sows (42.6%). Treatment did not affect the percentage of sows ovulating by 56 hours after treatment (p=0.10), however sows treated with triptorelin had a higher percentage of sows ovulating (average of 80.4%) than sows treated with vehicle (58.3%). While the average wean to ovulation interval did not differ between triptorelin treated and vehicle treated animals, a greater synchrony of ovulation was observed in triptorelin treated sows with 70-77% of sows ovulating during their most synchronous 24 hr period (120 to 144 hr after weaning) compared to vehicle treated sows with only 39.9% of sows ovulating during their most synchronous period (128 to 156 hours after weaning).

Example 7

Pregnancy Rate and Litter Size

Pregnancy rates, calculated as the percentage of animals allotted to each treatment group that were pregnant at slaughter, averaged 66.6% and did not differ significantly among treatment groups although pregnancy was numerically highest in triptorelin treated sows inseminated 18 hours following treatment (74.4%) followed by triptorelin treated sows inseminated at 24 hours following treatment (68.1%), triptorelin treated sows inseminated at 30 hours following treatment (62.3%) and placebo treated sows inseminated at 24 hours following treatment (61.8%). There was a tendency (p=0.09) for triptorelin treated sows inseminated at 18 hours (12.4 fetuses) and at 24 hours (11.8 fetuses) post treatment to have a higher number of healthy fetuses than triptorelin treated sows inseminated at 30 hours (8.6) post treatment and for vehicle treated sows inseminated at 24 hours (8.6) following treatment. The weight of healthy fetuses did not differ significantly among the treatment groups.

(OG24), or OVUGEL™ at 96 h post-weaning and a single AI 30 h later (OG30). OVUGEL™ was administered ~2 cm posterior to the cervix using the deposition catheter. Estrus detection was performed once daily from d 3 after weaning until d 7. Ultrasound was performed every 8 h from d 5 through d 6. On d 30 of gestation, the sows were sacrificed and reproductive tracts examined.

There was no effect of treatment on sows expressing estrus within 7 days of weaning (79%) or on the wean-to-estrus interval (4.7 days). The percentage of sows that ovulated by 48 h after treatment was greater (P=0.005) in OG18, OG24, and OG30 than in the Placebo treatment (Table 4). The interval from AI to ovulation was different among treatment groups (P<0.001, Table 4) and occurred furthest from ovulation for OG18, intermediate for Placebo and OG24, and closest for OG30. Pregnancy rates were not influenced by treatment (P=0.60, Table 4) but were influenced by interval from AI to ovulation (P=0.02). There was a significant effect of treatment (P=0.003) on the number of healthy fetuses at day 30 with more fetuses in OG18 and OG24 compared to the OG30 and Placebo treatments (Table 4). There was no effect of treatment on number of CL (P=0.30) but there was a tendency (P=0.09) for an effect on embryo survival (Table 4).

Results indicate that OVUGEL™ effectively synchronized ovulation without affecting pregnancy rate, and that litter size at day 30 of pregnancy was greater following a single AI at 18 or 24 hours after OVUGEL™ compared to AI at 30 h after OVUGEL™ or compared to single inseminations after Placebo treatment.

TABLE 3

Least squares means for response variable.

| | Placebo AI 24 | OG AI 18 | OG AI 24 | OG AI 30 | SEM | P |
|---|---|---|---|---|---|---|
| N | 31 | 32 | 32 | 32 | | |
| Estrus (%) | 81.5 | 81.5 | 78.3 | 75.7 | 7.50 | 0.94 |
| Wean to Estrus Interval (h) | 114.6 | 114.3 | 108.6 | 111.8 | 4.04 | 0.69 |
| Average Day 5 Follicle Size (mm) | 7.1 | 7.3 | 7.2 | 7.3 | 0.18 | 0.85 |
| Wean to Ovulation Interval (h) | 140.0 | 140.3 | 139.9 | 139.3 | 1.63 | 0.97 |
| Interval from AI to Ovulation (h) | 19.6$^x$ | 26.3$^y$ | 19.9$^x$ | 13.3$^z$ | 1.63 | 0.0001 |
| OV24 (%) | 2.7 | 2.7 | 0 | 5.8 | 3.14 | 0.58 |
| OV32 (%) | 15.3 | 8.9 | 12.1 | 13.4 | 5.95 | 0.89 |
| OV40 (%) | 31.3 | 27.9 | 31.0 | 27.7 | 8.19 | 0.98 |
| OV48 (%) | 42.6$^x$ | 74.0$^y$ | 77.0$^y$ | 76.8$^y$ | 8.00 | 0.0054 |
| OV56 (%) | 58.3 | 77.2 | 82.2 | 81.7 | 7.74 | 0.10 |
| Pregnant (%) | 61.8 | 74.4 | 68.1 | 62.3 | 8.07 | 0.66 |
| Number of Healthy Fetuses | 8.6 | 12.4 | 11.8 | 8.6 | 1.40 | 0.09 |
| Weight of Healthy Fetuses (g) | 1.5 | 1.6 | 1.6 | 1.6 | 0.04 | 0.17 |
| AIOVh Std err: | 1.8379 | 1.5804 | 1.5483 | 1.5700 | | |
| # Healthy Fetuses Std err: | 1.3966 | 1.3966 | 1.3968 | 1.4105 | | |

Means with differing superscripts within a row differ significantly at p = 0.05
Abbreviations are as follows: N (number of sows), Estrus (estrus during the period of Day 3 until Day 6), OV24 (percent sows ovulated at 24 hr after treatment), and Pregnant (pregnant sows of all sows allotted).

Example 8

Study 1

United Feeds Research Farm

Three study replicates were performed at an 800 sow research farm. All replicates included estrus and ovulation data and two replicates included AI, pregnancy and litter results. At weaning, mixed parity sows (n=32/treatment) received either vehicle carrier at 96 h post-weaning and a single AI 24 h later (Placebo), the test substance OVUGEL™ at 96 h post-weaning and a single AI 18 h later (OG18), OVUGEL™ at 96 h post-weaning and a single AI 24 h later

TABLE 4

Unadjusted means for treatment responses.

| | Placebo | OG18 | OG24 | OG30 | SE |
|---|---|---|---|---|---|
| Ovulate by 48 h, % | 40.6$^a$ | 71.9$^b$ | 75.0$^b$ | 75.0$^b$ | 4.2 |
| AI* to Ovulation (h) | 20.3$^a$ | 26.4$^b$ | 19.1$^a$ | 15.5$^c$ | 1.0 |
| Pregnant (%) | 68.2 | 86.4 | 81.8 | 68.2 | 4.6 |

TABLE 4-continued

Unadjusted means for treatment responses.

|  | Placebo | OG18 | OG24 | OG30 | SE |
|---|---|---|---|---|---|
| Fetuses | 12.9$^a$ | 16.5$^b$ | 17.4$^b$ | 12.6$^a$ | 0.6 |
| CL number | 18.5 | 22.1 | 23.0 | 17.6 | 1.2 |
| ES (%) | 53.2 | 65.9 | 67.3 | 57.0 | 2.4 |

AI = Artificial Insemination
CL = Corpora Lutea
ES = Embryo Survival
OG = OVUGEL ™

Example 9

Study 2

Bache Farm Study

Sows were weaned (Day 0) and screened for enrollment in the study, body condition recorded, and assigned to a treatment group. Postpartum sows, from parity 1 to 10, were blocked by lactation length, parity, and body condition score. No sows with a body condition score below 2.5 of above 3.5 was used. Genotypes used were those typically used in commerce in the U.S. and Canada. Treatment groups were stalled in areas separate from each other so that those sows bred later in the day did not receive multiple sessions of boar exposure. Each treatment sow received a single dose of the triptorlein composition (OVUGEL™) on Day 4 post-weaning. Control sows were untreated.

Estrus detection was performed once daily between Days 18-24 following insemination to determine if the sows had recycled. Sows that have returned to estrus were recorded and then rebred following normal farm SOP (these animals were off the study but subject to the withdrawal period). Transabdominal ultrasound (once) to confirm pregnancy in sows that had not returned to estrus was performed 28 to 32 days after insemination. The withdrawal period was verified 51 days post treatment. The date of farrowing, number of live born pigs and number of stillborn pigs within 24 hours after birth were recorded. Piglets were fostered according to usual farm protocols.

At least 90 sows were allocated to each of the following groups. Controls were untreated. All other sows were given OVUGEL™ containing 200 µg triptorelin, as the acetate.

1) Controls: Untreated and inseminated at intervals following detection of estrus as is normally practiced on each site;
2) Triptorelin: Inseminated once at 15 hr (+/−0.5 hrs) after triptorelin treatment;
3) Triptorelin: Inseminated once at 18 hr (+/−0.5 hrs) after triptorelin treatment;
4) Triptorelin: Inseminated once at 21 hr (+/−0.5 hrs) after triptorelin treatment;
5) Triptorelin: Inseminated once at 24 hr (+/−0.5 hrs) after triptorelin treatment;
6) Triptorelin: Inseminated once at 27 hr (+/−0.5 hrs) after triptorelin treatment.

TABLE 5

Time of Insemination Following OvuGel Administration

|  | Bred Farm SOP | Bred 15 hrs Post OvuGel ™ | Bred 18 hrs Post OvuGel ™ | Bred 21 hrs Post OvuGel ™ | Bred 24 hrs Post OvuGel ™ | Bred 27 hrs Post OvuGel ™ | Std Err Means | Contrast, Treatment P< |
|---|---|---|---|---|---|---|---|---|
| Returns At 21 d, % | 19.46$^{ab}$ | 7.94 $^b$ | 7.99 $^b$ | 19.72$^{ab}$ | 16.18 $^{ab}$ | 22.74 $^a$ | 4.5420 | 0.09 |
| Pregnant At 28 d, % | 79.28$^{bc}$ | 80.80 $^c$ | 82.55 $^c$ | 60.66 $^a$ | 71.08$^{abc}$ | 64.52$^{ab}$ | 5.5913 | 0.03 |
| % Farrow Of Wean | 75.83 $^b$ | 77.32 $^b$ | 79.11 $^b$ | 59.44 $^a$ | 67.63 $^{ab}$ | 59.44 $^a$ | 5.7977 | 0.04 |
| Total Born | 12.27 | 11.84 | 13.10 | 12.39 | 12.15 | 12.59 | 0.5563 | 0.65 |
| Born Alive | 11.15 | 10.19 | 11.48 | 10.84 | 10.41 | 11.13 | 0.6030 | 0.62 |
| Stillborn | 1.13 | 1.65 | 1.62 | 1.56 | 1.74 | 1.47 | 0.3780 | 0.88 |
| Mummies | 0.51 $^b$ | 0.28$^{ab}$ | 0.27$^{ab}$ | 0.11 $^a$ | 0.36 $^{ab}$ | 0.40$^{ab}$ | 0.1110 | 0.21 |

Data were collected from 366 sows (61 sows per treatment).
LS means calculated using the PROC GLM procedure of SAS and assumed a model with treatment and cohort.
There was no treatment by cohort interaction for any of the variables tested.
LS means with different superscripts differ at P < 0.05.

Estrus detection was performed on Day 4, and continued once a day until 4 days after treatment (Day 8) or until sows no longer showed estrus. Control sows (untreated) were inseminated at intervals following detection of estrus as is normally practiced at the farm. OVUGEL™ treated sows were inseminated with a single insemination at 15 hours (6:00 am+/−0.5 hr), 18 hours (9:00 am+/−0.5 hr), 21 hours (12:00 pm+/−0.5 hr), 24 hours (3:00 pm+/−0.5 hr), and 27 hours (6:00 pm+/−0.5 hr) post treatment.

Example 10

Hormone Stability

Figure 2:
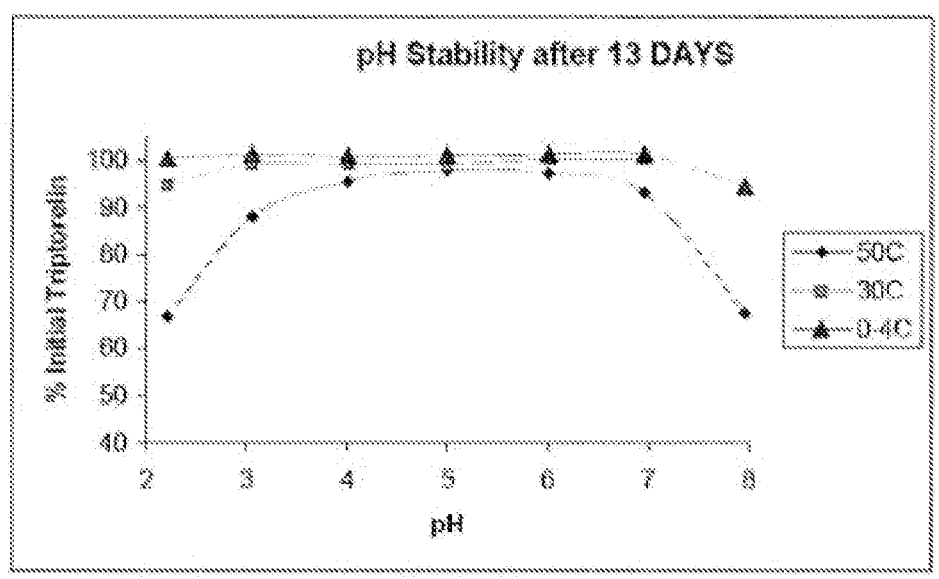
FIG. 2. shows triptorelin stability after 13 days at 0-4° C. (triangle), 30° C. (square), and 50° C. (diamond).

FIG. 2 shows triptorelin stability (250 µg per mL$^{-1}$). The effect of pH was analyzed at 0-4° C., 30° C., and 50° C. (McIlvaine buffer). FIG. 2 shows an optimal pH range of about 5 to about 6 for hormone stability.

Example 11

Stabilizer Analysis

The stability of formulations containing various stabilizers were studied at a 3-month time point. The data summarized in Table 6 indicates that L-Methionine provided the most stable formulation.

TABLE 6

Stability summary of formulations containing stabilizers

| Stabilizer | Formulation F-0 | Condition (° C.) | % Label Claim | % TA (as peak area) | Total Rel Subs (each >0.15%) |
|---|---|---|---|---|---|
| None (Control) | 11 | 25 | 94% | 96% | 2.6% |
|  |  | 50 | 43% | 71% | 28.8% |
| EDTA 0.02% | 17 | 2-8 | 98% | 98% | 0.5% |
|  |  | 25 | 94% | 97% | 1.8% |
|  |  | 50 | 78% | 89% | 10.7% |
| L-methionine (0.1%) | 18 | 2-8 | 102% | 99% | None > 0.3% |
|  |  | 25 | 89% | 88% | 0.7% |
|  |  | 50 | 87% | 90% | 0.3% |
| EDTA/L-methionine (0.02/0.1%) | 23 | 2-8 | 101% | 98% | 0.7% |
|  |  | 25 | 98% | 88% | 0.7% |
|  |  | 40 | 91% | 84% | 4.7% |
|  |  | 50 | 79% | 90% | 8.9% |
| Mannitol (3%) | 25 | 2-8 | 98% | 98% | 0.7% |
|  |  | 40 | 89% | 94% | 6.6% |
|  |  | 50 | 76% | 87% | 11.0% |
| EDTA/L-methionine/D-Mannitol (0.02/0.1/3%) | 26 | 2-8 | 98% | 99% | 0.4% |
|  |  | 40 | 88% | 94% | 5.0% |
|  |  | 50 | 78% | 88% | 11.4% |
| EDTA/L-methionine/D-Mannitol/P-80 (0.02/0.1/3/0.1%) | 27 | 2-8 | 95% | 96% | 0.3% |
|  |  | 40 | 85% | 95% | 4.4% |
|  |  | 50 | 73% | 88% | 10.9% |

Where P-80 is polycarbonate 80

Example 12

Method of Preparing Hormone Composition

In one method of preparation embodiment, the hormone is dissolved in a vessel containing citric acid and water, but separate from the other ingredients. The other ingredients are then added to the hormone composition, and water is added before addition of the methylcellulose composition. The methylcellulose composition is added slowly with high shear mixing to ensure homogeneity of the composition and to avoid clumping.

Example 13

Timed Insemination Following Intravaginal GnRH Agonist Treatment in Postpartum Sows This study shows the effect of a single, fixed timed insemination following GnRH administration on subsequent farrowing rate and litter size as compared to control sows bred at onset of estrus and daily for the duration of estrus (Table 7 and 8). One hundred ninety-nine weaned sows (PIC) were blocked by parity (parities 1 through 6; average parity 2.9), previous lactation length (range 13 to 23 d; average length 19 d), and body condition score (range 2.0 to 4.0; average score 3.1) and allocated to one of two treatments. Control sows were observed for behavioral estrus for 7 d after weaning and inseminated the day they were observed in estrus and at 24 h intervals for the duration of estrus. Sows in the GnRH treatment group (GnRH sows) were administered intravaginally with the GnRH agonist preparation (OvuGel™), described in Examples 2 and 3, in the morning four days after weaning and inseminated once 21-22 h after OvuGel™ treatment. The GnRH sows were also observed for 7 d after weaning for signs of behavioral estrus but were inseminated without regard to signs of standing estrus.

Of the 99 Control sows, 90.9% (90) were bred by 7 d post-weaning compared to 100% (100) of the GnRH sows (P<0.01). Control sows averaged 2.1 inseminations per sow while GnRH sows all had 1 insemination per sow (P<0.01). There was no difference (P>0.75) in number of sows farrowing between Control and GnRH sows, 79.2% (79 sows) and 80.7% (81 sows), respectively. There was no effect of treatment on number of stillborns (P>0.45) and mummies (P>0.15). GnRH sows farrowed an average of 11.2 pigs born alive compared to 11.4 pigs born alive to Control sows (P>0.65). Pigs born per semen dose was 5.2 vs. 9.6 (P<0.01) for Control and GnRH sows, respectively. These data indicate that treating sows with OvuGel™ and inseminating once following treatment results in farrowing rates and litter sizes comparable to sows receiving multiple inseminations during behavioral estrus, and a higher number of pigs born per semen dose for the OvuGel™-treated animals.

TABLE 7

Responses to treatment and comparisons between Control and GnRH sows [1]

|  | Control | GnRH |
|---|---|---|
| Number of Sows Allotted | 99 | 100 |
| Wean to Estrus Interval, d | 4.4 | 4.3 |
| In Estrus at Insemination, % | 100 | 90 |
| No. Inseminated by 7 d post-weaning | 90 | 100 |
| Doses of Semen per Sow Inseminated | 2.1 | 1.0 |
| Returns at 21 d of Sows Inseminated, % | 6.7 | 8 |
| No. Returns at 21 d | 6 | 8 |
| Pregnant at 30 d of Sows Allotted, % | 81.8 | 85 |
| No. Pregnant at 30 d | 81 | 85 |
| No. Sows Farrowed | 79 | 81 |
| Sows Farrowed of Sows Allotted, % | 79.8 | 81.0 |
| Total Born per Litter | 12.1 | 11.8 |
| Total Born per Semen Dose | 5.3 | 9.6 |
| Born Alive per Litter | 11.4 | 11.2 |
| Stillborn per Litter | 0.7 | 0.6 |
| Mummies per Litter | 0.8 | 0.6 |
| Piglet Index (Pigs Born Alive/100 Sows Allotted) | 906 | 909 |

[1] GnRH sows were treated between 99 and 102 hours following weaning and inseminated between 21 and 22 hours post treatment. Control sows were untreated and bred normally. Numbers in the table are unadjusted means and raw numbers.

TABLE 8

Responses to treatment (LS means ± SEM) and comparisons between Control and GnRH sows[1]

|  | Control | GnRH | SEM | Contrast, P< |
|---|---|---|---|---|
| Sows Allocated to Treatments | 99 | 100 | * | * |
| Sows Inseminated in 7-d period after weaning | 90 | 100 | * | * |
| Sows In Estrus at AI (%) | 100 | 90.0 | 2.28 | 0.005 |
| Weaning-to-.Estrus Interval (d) | 4.4 | 4.3 | 0.06 | 0.33 |
| No. of Inseminations/Sow | 2.1 | 1.0 | 0.02 | 0.0001 |
| Sows Pregnant of Sows Allotted (%) | 81.4 | 84.8 | 3.74 | 0.52 |
| No. Sows Farrowed | 79 | 81 | * | * |
| Sows Farrowed of Sows Allotted (%) | 79.2 | 80.7 | 3.94 | 0.78 |
| Total Pigs Born/Semen Dose | 5.2 | 9.6 | 0.45 | 0.0001 |
| Total Pigs Born Alive (all litters) | 901 | 910 | * | * |

TABLE 8-continued

Responses to treatment (LS means ± SEM)
and comparisons between Control and GnRH sows[1]

|  | Control | GnRH | SEM | Contrast, P< |
|---|---|---|---|---|
| Total Pigs Born/Litter | 12.1 | 11.8 | 0.36 | 0.56 |
| Pigs Born Alive/Litter | 11.4 | 11.2 | 0.34 | 0.67 |

[1] Data collected from 199 sows (99 Control, 100 GnRH). Control sows were bred following normal farm SOP. GnRH sows were treated on d 4 post-weaning and inseminated once 21-22 hrs later. LS means calculated using the PROC MIX procedure of SAS and assumed a model with treatment and cohort. There was no treatment by cohort interaction for any of the variables tested.

Example 14

Timed Insemination Following GnRH Agonist Administration in Weaned Sows

This study shows the effect of a single, fixed timed insemination following GnRH administration on subsequent farrowing rate and litter size (Tables 9 and 10). Three hundred weaned sows (PIC) were blocked by parity (parities 1 through 6; average parity 2.8), previous lactation length (range 17 to 25 d; average length 21 d), and body condition score (range 2.5 to 3.5; average score 2.8) and allocated to one of two treatments. Control sows were observed for 7 d after weaning for behavioral estrus and inseminated the day they were observed in estrus and at 24 h intervals for the duration of estrus. Sows in the GnRH treatment group (GnRH sows) were also observed for 7 d after weaning for signs of behavioral estrus but were treated intravaginally with the GnRH agonist preparation (OvuGel™), described in Examples 2 and 3, on d 4 after weaning and then inseminated once 24±2 h post-OvuGel™ treatment, regardless of whether or not they showed signs of standing estrus. Of the 150 Control sows, 80.7% (121) were bred by 7 d post-weaning compared to 100% (150) of the GnRH sows (P<0.01).

Control sows averaged 2.3 inseminations per sow while GnRH sows all had 1 insemination per sow (P<0.01). There was no difference (P>0.40) in number of sows farrowing between Control and GnRH sows, 72.7% (109 sows) and 76.7% (115 sows), respectively. There was no effect of treatment on number of stillborns (P>0.30) and mummies (P>0.45). GnRH sows farrowed an average of 11.3 pigs born alive compared to 10.9 pigs born alive to Control sows (P<0.37). Pigs born per semen dose was 5.6 vs. 9.6 (P<0.01) for Control and GnRH sows, respectively. These data indicate that treating sows with the GnRH agonist, OvuGel™ and inseminating once with respect to the time of GnRH treatment results in farrowing rates and litter sizes comparable to sows receiving multiple inseminations during behavioral estrus. The results also show that a higher amount of pigs are born per semen dose for the OvuGel™-treated animals than the control animals.

TABLE 9

Responses to treatment and comparisons
between Control and GnRH sows[1]

|  | Control | GnRH |
|---|---|---|
| Number of Sows Allotted | 150 | 150 |
| Wean to Estrus Interval, d | 4.4 | 4.4 |
| In Estrus at Insemination, % | 100 | 84 |
| No. Inseminated by 7 d post-weaning | 121 | 150 |
| No. Inseminated 8 to 15 d post-weaning | 5 | . |
| Doses of Semen per Sow Inseminated | 2.2 | 1.0 |
| Returns at 21 d of Sows Inseminated, % | 3.3 | 8.7 |
| No. Returns at 21 d | 4 | 13 |
| Pregnant at 30 d of Sows Allotted, % | 74.0 | 80.0 |
| No. Pregnant at 30 d | 111 | 120 |
| No. Sows Farrowed | 109 | 115 |
| Sows Farrowed of Sows Allotted, % | 72.7 | 76.7 |
| Total Born per Litter | 12.2 | 12.6 |
| Total Born per Semen Dose | 5.6 | 9.6 |
| Born Alive per Litter | 10.9 | 11.3 |
| Stillborn per Litter | 1.0 | 0.9 |
| Mummies per Litter | 0.3 | 0.4 |
| Piglet Index (Pigs Born Live/100 Sows Allotted) | 794 | 867 |

[1] Sows were treated at 96 hours following weaning and inseminated 24 ± 2 hours later on d 5 post-weaning (120 to 122 hr post-weaning). Control sows were untreated and bred normally. Numbers in the table are unadjusted means and raw numbers.

TABLE 10

Responses to treatment (LS means ± SEM)
and comparisons between Control and GnRH sows[1]

|  | Control | GnRH | SEM | Contrast, P< |
|---|---|---|---|---|
| Sows Allocated to Treatments | 150 | 150 | * | * |
| Sows Inseminated in 7-d period after weaning | 121 | 150 | * | * |
| Sows In Estrus at AI (%) | 100 | 84.0 | 2.34 | 0.0001 |
| Weaning-to-Estrus Interval (d) | 4.4 | 4.4 | 0.05 | 0.75 |
| No. of Inseminations/Sow | 2.3 | 1.0 | 0.04 | 0.0001 |
| Sows Pregnant of Sows Allotted (%) | 74.0 | 80.0 | 3.44 | 0.22 |
| No. Sows Farrowed | 109 | 115 | * | * |
| Sows Farrowed of Sows Allotted (%) | 72.7 | 76.7 | 3.56 | 0.43 |
| Total Pigs Born/Semen Dose | 5.6 | 9.6 | 0.43 | 0.0001 |
| Total Pigs Born Alive (all litters) | 1191 | 1300 | * | * |
| Total Pigs Born/Litter | 12.2 | 12.6 | 0.31 | 0.41 |
| Pigs Born Alive/Litter | 10.9 | 11.3 | 0.29 | 0.37 |

[1] Data collected from 300 sows (150 Control, 150 GnRH). Control sows were bred following normal farm SOP. GnRH sows were treated on d 4 post-weaning and inseminated once 24 +/− 2 hrs later. LS means calculated using the PROC MIX procedure of SAS and assumed a model with treatment and cohort. There was no treatment by cohort interaction for any of the variables tested.

Example 15

Statistical Analysis

These data were analyzed using the Proc MIXED and General linear models procedures of SAS (Cary, N.C.) for continuous and discrete variables. For all analyses, the models contained the fixed effects of treatment (placebo controls inseminated 24 hours after treatment, triptorelin treated sows inseminated 18 hours after treatment, triptorelin treated sows inseminated 24 hours after treatment and triptorelin treated sows inseminated 30 hours after treatment) and replicate. The records for sow parity and lactation length were included as covariates. First order interaction of treatment and replicate was tested and removed when non-significant. Differences between treatments were tested on least squares means estimates using the T test at P<0.05.

What is claimed is:
1. A method of synchronizing ovulation and time of insemination in a swine, the method comprising the step of administering to the swine, on the fourth day after weaning, a dose of a hormone of the formula

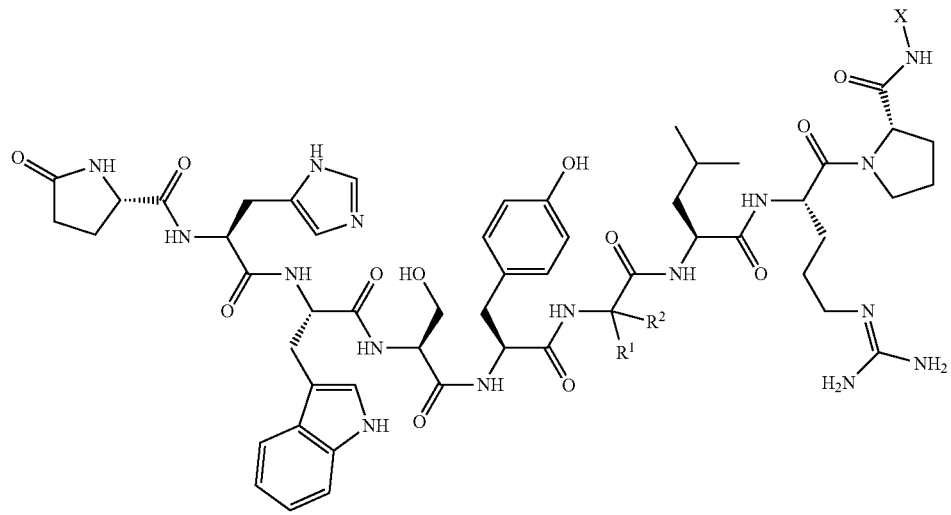

or a solvate, a hydrate, or a pharmaceutically acceptable salt thereof,
wherein $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;
X is hydrogen, or X is selected from the group consisting of, alkyl, cycloalkyl, heteroalkyl, optionally substituted alkylene-carboxamide; and
$HNC(O)NR^3R^4$, where $R^3$ and $R^4$ are in each instance independently selected from the group consisting of hydrogen, alkyl, heteroalkyl and haloalkyl,
wherein the swine is inseminated only one time about 15 to about 24 hours after administration of the hormone and wherein heat detection is not performed to synchronize ovulation of the swine.

2. The method of claim 1 wherein the hormone is a GnRH agonist.

3. The method of claim 2 wherein the GnRH agonist is triptorelin.

4. The method of claim 2 wherein the GnRH agonist is triptorelin acetate.

5. The method of claim 4 wherein the GnRH agonist is administered in a composition comprising a gel.

6. The method of claim 5 wherein the gel comprises a polysaccharide.

7. The method of claim 6 wherein the polysaccharide is a cellulose.

8. The method of claim 7 wherein the cellulose is methylcellulose.

9. The method of claim 8 wherein the swine is inseminated at about 22 hours after administration of the hormone.

10. The method of claim 9 wherein the swine is a postpartum sow.

11. The method of claim 10 wherein the hormone is administered to the swine using a deposition catheter.

12. The method of claim 11 wherein the insemination is an artificial insemination.

13. The method of claim 12 wherein 200 μg of the hormone is administered.

14. The method of claim 13 wherein the hormone is administered intravaginally.

15. The method of claim 14 wherein the hormone is administered into the anterior vagina.

16. The method of claim 1 wherein the hormone is administered by injection.

17. The method of claim 2 wherein the hormone is administered by injection.

18. The method of claim 3 wherein the hormone is administered by injection.

19. The method of claim 4 wherein the hormone is administered by injection.

20. The method of claim 16 wherein the swine is inseminated at about 22 hours after administration of the hormone.

21. The method of claim 17 wherein the swine is inseminated at about 22 hours after administration of the hormone.

22. The method of claim 18 wherein the swine is inseminated at about 22 hours after administration of the hormone.

23. The method of claim 19 wherein the swine is inseminated at about 22 hours after administration of the hormone.

24. The method of claim 20 wherein the swine is a postpartum sow.

25. The method of claim 21 wherein the swine is a postpartum sow.

26. The method of claim 22 wherein the swine is a postpartum sow.

27. The method of claim 23 wherein the swine is a postpartum sow.

28. The method of claim 1 wherein the swine is a postpartum sow.

29. The method of claim 1 wherein the swine is a gilt.

30. The method of claim 1 wherein the insemination is an artificial insemination.

31. The method of claim 1 wherein the hormone is administered in an effective amount and the effective amount of the hormone is about 10 μg to about 500 μg.

32. The method of claim 1 wherein the dose of the hormone is administered using a method selected from the group consisting of use of a deposition catheter, manual administration, and injection.

33. The method of claim 1 wherein the swine is inseminated about 18 to about 22 hours after administration of the hormone.

34. The method of claim 1 wherein the pregnancy rate of the swine and/or the number of healthy fetuses is increased relative to a swine to which no hormone is administered.

35. The method of claim 1 wherein the hormone is administered intravaginally.

36. The method of claim 35 wherein the hormone is administered into the anterior vagina.

37. The method of claim 1 wherein the hormone is a gonadotropin releasing hormone receptor agonist.

38. The method of claim 37 wherein the hormone is a triptorelin salt.

39. The method of claim 1 wherein the hormone is a gonadotropin releasing hormone and the hormone has the formula pGlu-His-Trp-Ser-Tyr-Gly-Leu-Arg-Pro-GlyNH$_2$.

40. The method of claim 1 wherein the hormone is in acetate form.

41. The method of claim 1 wherein the hormone is administered in a composition comprising a gel.

42. The method of claim 41 wherein the gel comprises a polysaccharide.

43. The method of claim 42 wherein the polysaccharide is a cellulose and the cellulose is methylcellulose.

44. The method of claim 1 wherein the hormone is administered with a stabilizer, and wherein the stabilizer is L-methionine.

45. The method of claim 1 or claim 15 wherein the swine is administered a single hormone.

46. A composition comprising triptorelin acetate and a gel, wherein the composition has a pH of about 5.0 to about 6.0.

47. The composition of claim 46 further comprising a stabilizer.

48. The composition of claim 47 wherein the stabilizer is L-methionine.

49. The composition of claim 48 wherein the gel comprises a polysaccharide.

50. The composition of claim 49 wherein the polysaccharide is a cellulose.

51. The composition of claim 50 wherein the polysaccharide is selected from the group consisting of celluloses, dextrans and alginates.

52. The composition of claim 51 wherein the cellulose is methylcellulose.

53. The composition of claim 52 wherein the gel comprises about 0.5 weight % to about 4.0 weight % of the methylcellulose.

54. The composition of claim 52 further comprising a preservative.

55. The composition of claim 54 wherein the preservative is selected from the group consisting of methylparaben and propylparaben.

56. The composition of claim 55 further comprising a tonicity agent.

57. The composition of claim 56 wherein the composition comprises 100 μg per mL of the triptorelin acetate.

58. The composition of claim 57 wherein the triptorelin acetate is in an effective amount of about 10 μg to about 500 μg.

59. A composition comprising methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methycellulose in an amount of about 1.2% weight per volume.

60. A kit comprising the composition of any one of claim 46, 48, 52, 55, 56, 57, or 59, wherein the kit further comprises a deposition catheter.

* * * * *